United States Patent

Fest et al.

Patent Number: 5,125,960
Date of Patent: Jun. 30, 1992

[54] HERBICIDAL SUBSTITUTED ARYLSULPHONYLAMINOGUANIDINOAZINES

[75] Inventors: Christa Fest, Wuppertal; Rolf Kirsten, Monheim; Joachim Kluth, Langenfeld; Klaus-Helmut Müller, Duesseldorf; Hans-Jochem Riebel, Wuppertal; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 561,857

[22] Filed: Aug. 1, 1990

[30] Foreign Application Priority Data

Aug. 23, 1989 [DE] Fed. Rep. of Germany ....... 3927770

[51] Int. Cl.⁵ ................. C07D 239/69; C07D 239/46; C07D 239/48; A01N 43/54
[52] U.S. Cl. ............................................ 71/92; 71/90; 544/321; 544/323; 544/324; 544/331; 544/332
[58] Field of Search .................. 71/92, 90; 544/321, 544/323, 324, 331, 332

[56] References Cited

U.S. PATENT DOCUMENTS 4,602,938 7/1986 Moriya et al. ...................... 71/92
4,725,303 2/1988 Moriya et al. ...................... 71/92

FOREIGN PATENT DOCUMENTS 0121082 10/1984 European Pat. Off.
0302378 2/1989 European Pat. Off.

Primary Examiner—John M. Ford
Attorney, Agent, or Firm—Sprung Horn Kramer & Woods

[57] ABSTRACT

Herbicidal substituted arylsulphonylaminoguanidinoazines of the formula

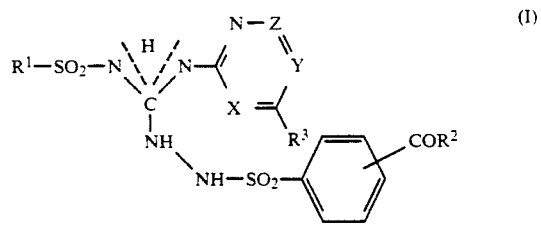

in which $R^1$ represents in each case optionally substituted aryl, aralkyl or heteroaryl, $R^2$ represents hydroxyl or amino, or represents in each case optionally substituted alkoxy or alkylamino, $R^3$ represents hydrogen, halogen, hydroxyl, alkyl, halogenoalkyl, alkoxyalkyl, alkoxy, halogenoalkoxy, alkylthio, halogenoalkylthio, amino, alkylamino or dialkylamino, X represents nitrogen or a —CH group, Y represents nitrogen or a —$CR^4$ group, where $R^4$ represents hydrogen, halogen, cyano, alkyl, formyl, alkyl-carbonyl or alkoxy-carbonyl, and Z represents nitrogen or a —$CR^5$ group, where $R^5$ represents hydrogen, halogen, hydroxyl, alkyl, alkoxy, alkylthio, alkylamino or dialkylamino, with the exception of the compound N'-(4,6-dimethylpyrimidin-2-yl)-N''-(2-methoxycarbonyl-phenylsulphonylamino)-N'''-(2-methoxycarbonyl-phenylsulphonyl)guanidine.

10 Claims, No Drawings

HERBICIDAL SUBSTITUTED ARYLSULPHONYLAMINOGUANIDINOAZINES

The invention relates to new substituted arylsulphonylaminoguanidinoazines, to processes for their preparation, and their use as herbicides.

It has already been disclosed that certain sulphonylaminoguanidinoazines, such as, for example, N'-(4,6-dimethyl-pyrimidin-2-yl)-N'-(4-methyl-phenyl-sulphonylamino)-N'''-(2-chloro-phenylsulphonyl)-guanidine and N'-(4,6-dimethyl-pyrimidin-2-yl)-N',-(2-methoxycarbonyl-phenylsulphonylamino)-N'''-(2-methoxycarbonylphenylsulphonyl)-guanidine, have herbicidal properties (cf. EP-A 121,082 and EP-A 302,378). However, the herbicidal action of these known compounds is not satisfactory in all respects.

New substituted arylsulphonylaminoguanidinoazines of the general formula (I)

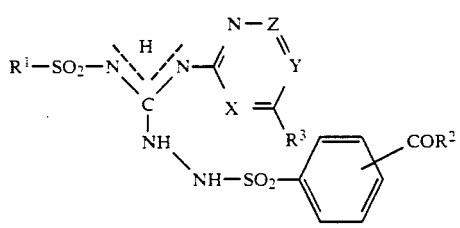

in which

R$^1$ represents in each case optionally substituted aryl, aralkyl or heteroaryl, R$^2$ represents hydroxyl or amino, or represents in each case optionally substituted alkoxy or alkylamino, R$^3$ represents hydrogen, halogen, hydroxyl, alkyl, halogenoalkyl, alkoxyalkyl, alkoxy, halogenoalkoxy, alkylthio, halogenoalkylthio, amino, alkylamino or dialkylamino, X represents nitrogen or a —CH group, Y represents nitrogen or a —CR$^4$ group, where R$^4$ represents hydrogen, halogen, cyano, alkyl, formyl, alkyl-carbonyl or alkoxy-carbonyl, and Z represents nitrogen or a —CR$^5$ group, where R$^5$ represents hydrogen, halogen, hydroxyl, alkyl, alkoxy, alkylthio, alkylamino or dialkylamino, have now been found, with the exception of N'-(4,6-dimethyl-pyrimidin-2-yl)-N'-(2-methoxycarbonyl-phenylsulphonylamino)-N'''-(2-methoxycarbonyl-phenylsulphonyl)guanidine —disclosed in EP-A 302,378.

The general formula (I) represents the individual tautomers which are possible, of the formulae (IA), (IB) and (IC)

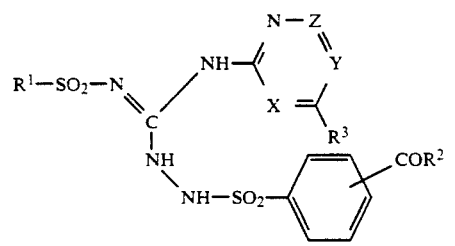

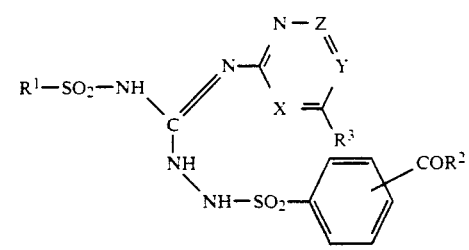

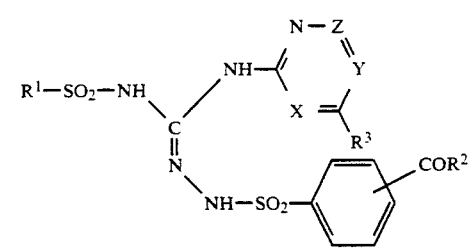

as well as mixtures of these tautomers.

The new substituted arylsulphonylaminoguanidinoazines of the general formula (I) are obtained when (a) sulphonyl compounds of the general formula (II)

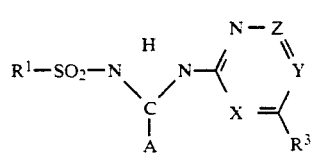

in which

R$^1$, R$^3$, X, Y and Z have the abovementioned meanings and

A represents one of the leaving groups

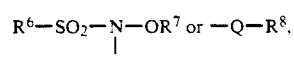

where

R$^6$ has the meaning indicated above in the case of R$^1$, but does not have to be identical to R$^1$ in each individual case, R$^7$ represents alkyl, alkenyl or aralkyl, R$^8$ represents alkyl, aralkyl or aryl, and Q represents oxygen or sulphur, are reacted with sulphonic acid hydrazides of the general formula (III)

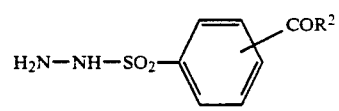

in which

R$^2$ has the abovementioned meaning, if appropriate in the presence of a diluent, or when b) aminoguanidinoazines of the general formula (IV)

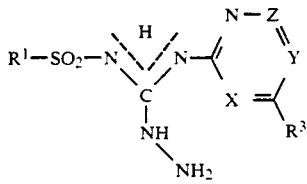

in which

R¹, R³, X, Y and Z have the abovementioned meanings, are reacted with sulphonyl halides of the general formula (V)

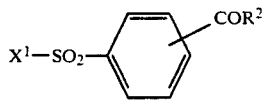

in which

R² has the abovementioned meaning, and
X¹ represents halogen,
or with sulphobenzoic anhydride of the formula (VI)

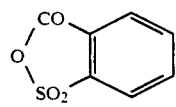

if appropriate in the presence of a diluent and if appropriate in the presence of an acid acceptor, or when (c) substituted arylsulphonylaminoguanidinoazines of the general formula (I) in which R² represents optionally substituted alkoxy and R¹, R³, X, Y and Z have the abovementioned meanings, are reacted with aqueous alkali metal hydroxide solutions or with ammonia or with optionally substituted alkylamines, if appropriate in the presence of a diluent.

The new substituted arylsulphonylaminoguanidinoazines of the general formula (I) are distinguished by a powerful herbicidal activity.

Surprisingly, the new compounds of the general formula (I) show a considerably better action, in particular a markedly better tolerance by crop plants, than the abovementioned, previously known sulphonylaminoguanidinoazines, which are comparable substances as far as their structure and profile of action are concerned.

The invention preferably relates to compounds of the formula (I) in which

R¹ represents the radical

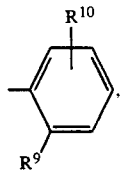

where

R⁹ and R¹⁰ are identical or different and represent hydrogen, fluorine, chlorine, bromine, iodine, cyano, nitro, $C_1-C_6$-alkyl (which is optionally substituted by fluorine, chlorine, bromine, cyano, carboxyl, $C_1-C_4$-alkoxycarbonyl, $C_1-C_4$-alkylamino-carbonyl, di-($C_1-C_4$-alkyl)-aminocarbonyl, hydroxyl, $C_1-C_4$-alkoxy, formyloxy, $C_1-C_4$-alkyl-carbonyloxy, $C_1-C_4$-alkoxycarbonyloxy, $C_1-C_4$-alkylamino-carbonyloxy, $C_1-C_4$-alkylthio, $C_1-C_4$-alkylsulphinyl, $C_1-C_4$-alkylsulphonyl, Di-($C_1-C$-alkyl)-aminosulphonyl, $C_3-C_6$-cycloalkyl or phenyl), or represent $C_2-C_6$-alkenyl (which is optionally substituted by fluorine, chlorine, bromine, cyano, $C_1-C_4$-alkoxy-carbonyl, carboxyl or phenyl), or represent $C_2-C_6$-alkinyl (which is optionally substitued by fluorine, chlorine, bromine, cyano, $C_1-C_4$-alkoxy-carbonyl, carboxyl or phenyl), or represent $C_1-C_4$-alkoxy (which is optionally substituted by fluorine, chlorine, bromine, cyano, carboxyl, $C_1-C_4$-alkoxy-carbonyl, $C_1-C_4$-alkoxy, $C_1-C_4$-alkylthio, or $C_1-C_4$-alkylsulphinyl or $C_1-C_4$-alkylsulphonyl), or represent $C_1-C_4$-alkylthio (which is optionally substituted by fluorine, chlorine, bromine, cyano, carboxyl, $C_1-C_4$-alkoxy-carbonyl, $C_1-C_4$-alkylthio, $C_1-C_4$-alkylsulphinyl or $C_1-C_4$-alkylsulphonyl), or represent $C_3-C_6$-alkenyloxy (which is optionally substituted by fluorine, chlorine, bromine, cyano or $C_1-C_4$-alkoxy-carbonyl, or represent $C_2-C_6$-alkenylthio (which is optionally substituted by fluorine, chlorine, bromine, cyano, nitro, $C_1-C_3$-alkylthio or $C_1-C_4$-alkoxycarbonyl), $C_3-C_6$-alkinyloxy or $C_3-C_6$-alkinylthio, or represent the radical —S(O)$_p$—R¹¹, where p represents the number 1 or 2, and R¹¹ represents $C_1-C_4$-alkyl (which is optionally substituted by fluorine, chlorine, bromine, cyano or $C_1-C_4$-alkoxy-carbonyl), $C_3-C_6$-alkenyl, $C_3-C_6$-alkinyl, $C_1-C_4$-alkoxy, $C_1-C_4$-alkoxy-$C_1-C_4$-alkylamino, $C_1-C_4$-alkylamino or di-($C_1-C_4$-alkyl)amino, or represents the radical —NHOR¹², where R¹² represents $C_1-C_{12}$-alkyl (which is optionally substituted by fluorine, chlorine, cyano, $C_1-C_4$-alkoxy, $C_1-C_4$-alkylthio, $C_1-C_4$-alkylsulphinyl, $C_1-C_4$-alkylsulphonyl, $C_1-C_4$-alkyl-carbonyl, $C_1-C_4$-alkoxy-carbonyl, $C_1-C_4$-alkylaminocarbonyl or di-($C_1-C_4$-alkyl)-aminocarbonyl), or represents $C_3-C_6$-alkenyl (which is optionally substituted by fluorine, chlorine or bromine), $C_3-C_6$-alkinyl, $C_3-C_6$-cycloalkyl, $C_3-C_6$-cycloalkyl-$C_1-C_2$-alkyl, phenyl-$C_1-C_2$-alkyl (which is optionally substituted by fluorine, chlorine, nitro, cyano, $C_1-C_4$-alkyl, $C_1-C_4$-alkoxy or $C_1-C_4$-alkoxycarbonyl), or represents benzylhydryl, or represents phenyl (which is optionally substituted by fluorine, chlorine, nitro, cyano, $C_1-C_4$-alkyl, trifluoromethyl, $C_1-C_4$-alkoxy, $C_1-C_2$-fluoroalkoxy, $C_1-C_4$-alkylthio, trifluoromethylthio or $C_1-C_4$-alkoxy-carbonyl), R⁹ and R¹⁰ furthermore represent phenyl or phenoxy, or represent amino, $C_1-C_4$-alkylcarbonylamino, $C_1-C_4$-alkoxy-carbonylamino, $C_1-C_4$-alkylamino-carbonylamino or di-($C_1-C_4$-alkyl)-amino-carbonylamino, or represent the radical —CO—R¹³, where R¹³ represents $C_1-C_6$-alkyl, $C_1-C_6$-alkoxy, $C_3-C_6$-cyclo-alkoxy, $C_3-C_6$-alkenyloxy, $C_1-C_4$-alkylthio, $C_1-C_4$-alkylamino, $C_1-C_4$-alkoxyamino, $C_1-C_4$-alkoxy-$C_1-C_4$-alkyl-amino or di-($C_1-C_4$-alkyl)-amino (each of which is optionally substituted by fluorine and/or chlorine), R₉ and R¹⁰ furthermore represent $C_1-C_4$-alkylsulphonyloxy, di-($C_1-C_4$-alkyl)-aminosulphonylaminoorthiazolyloxy, or represent the radical —CH=N—R¹⁴, where R¹⁴ represents $C_1-C_6$-alkyl which is optionally substituted by fluorine, chlorine, cyano, carboxyl, $C_1-C_4$-alkoxy, $C_1-C_4$-alkylthio, $C_1-C_4$-alkylsulphinyl or $C_1-C_4$-alkylsulphonyl, or represents benzyl which is optionally substituted by fluorine or chlorine, or represents $C_3-C_6$-alkenyl or $C_3-C_6$-alkinyl, each of which is optionally substituted by fluorine or chlorine, or represents phenyl which is optionally substituted by fluorine, chlorine, bromine, $C_1-C_4$-alkyl, $C_1-C_4$-alkoxy, trifluoromethyl, trifluoromethoxy or trifluoromethylthio, or represents $C_1-C_6$-alkoxy, $C_3-C_6$-alkenoxy, $C_3-C_6$-alkinoxy or benzyloxy, each of which is optionally substituted by fluorine and/or chlorine, or represents amino, $C_1-C_4$-alkylamino, di-($C_1-C_4$-alkyl)-amino, phenylamino, $C_1-C_4$-alkylcarbonyl-amino, $C_1-C_4$-alkoxy-carbonylamino or $C_1-C_4$-alkyl-sulphonylamino, or represents phenylsulphonylamino which is optionally substituted by fluorine, chlorine, bromine or methyl, furthermore $R^1$ represents the radical

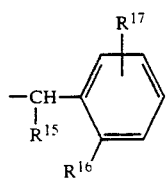

where $R^{15}$ represents hydrogen or $C_1-C_4$-alkyl, $R^{16}$ and $R^{17}$ are identical or different and represent hydrogen, fluorine, chlorine, bromine, nitro, cyano, $C_1-C_4$-alkyl (which is optionally substituted by fluorine and/or chlorine), $C_1-C_4$-alkoxy (which is optionally substituted by fluorine and/or chlorine), carboxyl, $C_1-C_4$-alkoxy-carbonyl, $C_1-C_4$-alkylsulphonyl or di-($C_1-C_4$-alkyl)-aminosulphonyl; furthermore $R^1$ represents the radical

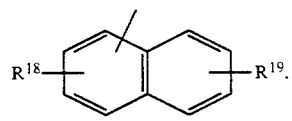

where $R^{18}$ and $R^{19}$ are identical or different and represent hydrogen, fluorine, chlorine, bromine, nitro, cyano, $C_1-C_4$-alkyl (which is optionally substituted by fluorine and/or chlorine) or $C_1-C_4$-alkoxy (which is optionally substituted by fluorine and/or chlorine); furthermore $R^1$ represents the radical

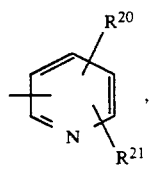

where $R^{20}$ and $R^{21}$ are identical or different and represent hydrogen, fluorine, chlorine, bromine, nitro, cyano, $C_1-C_4$-alkyl (which is optionally substituted by fluorine and/or chlorine), $C_1-C_4$-alkoxy (which is optionally substituted by fluorine and/or chlorine), or represent $C_1-C_4$-alkylthio, $C_1-C_4$-alkylsulphinyl or $C_1-C_4$-alkylsulphonyl (each of which is optionally substituted by fluorine and/or chlorine), and also represent di-($C_1-C_4$-alkyl)-aminocarbonyl or $C_1-C_4$-alkoxy-carbonyl; furthermore $R^1$ represents the radical

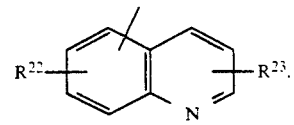

where $R^{22}$ and $R^{23}$ are identical or different and represent hydrogen, fluorine, chlorine, bromine, $C_1-C_4$-alkyl (which is optionally substituted by fluorine and/or bromine) or $C_1-C_4$-alkoxy (which is optionally substituted by fluorine and/or chlorine), or represent $C_1-C_4$-alkylthio, $C_1-C_4$-alkylsulphinyl or $C_1-C_4$-alkylsulphonyl (each of which is optionally substituted by fluorine and/or chlorine), or represent di-($C_1-C_4$-alkyl)aminosulphonyl; furthermore $R^1$ represents the radical

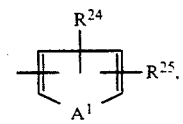

where $R^{24}$ and $R^{25}$ are identical or different and represent hydrogen, fluorine, chlorine, bromine, cyano, nitro, $C_1-C_4$-alkyl (which is optionally substituted by fluorine and/or chlorine), $C_1-C_4$-alkoxy (which is optionally substituted by fluorine and/or chlorine), $C_1-C_4$-alkylthio, $C_1-C_4$-alkylsulphinyl or $C_1-C_4$-alkylsulphonyl (which is optionally substituted by fluorine and/or chlorine), di-($C_1-C_4$-alkyl)-amino-sulphonyl or $C_1-C_4$-alkoxycarbonyl, and $A^1$ represents oxygen, sulphur or the group $N-Z^1$, where $Z^1$ represents hydrogen, $C_1-C_4$-alkyl (which is optionally substituted by fluorine, chlorine, bromine or cyano), $C_3-C_6$-cycloalkyl, benzyl, phenyl (which is optionally substituted by fluorine, chlorine, bromine or nitro), $C_1-C_4$-alkylcarbonyl, $C_1-C_4$-alkoxy-carbonyl or di-($C_1-C_4$-alkyl)-aminocarbonyl; furthermore $R^1$ represents the radical

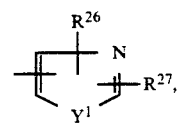

where $R^{26}$ represents hydrogen, $C_1-C_5$-alkyl or halogen, $R^{27}$ represents hydrogen or $C_1-C_5$-alkyl, and $Y^1$ represents sulphur or the group $N-R^{28}$, where $R^{28}$ represents hydrogen or $C_1-C_5$-alkyl, furthermore $R^1$ represents the radical

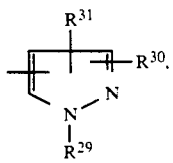

where
$R^{29}$ represents hydrogen, $C_1-C_4$-alkyl, phenyl, naphthyl or (iso)quinolinyl, $R^{30}$ represents hydrogen, halogen, cyano, nitro, $C_1-C_4$-alkyl (which is optionally substituted by fluorine and/or chlorine), $C_1-C_4$-alkoxy (which is optionally substituted by fluorine and/or chlorine) or $C_1-C_4$-alkoxycarbonyl, and $R^{31}$ represents hydrogen, halogen or $C_1-C_4$-alkyl, furthermore $R^1$ represents the radical

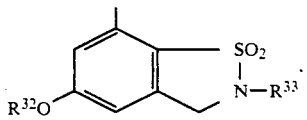

where
$R^{32}$ represents $C_1-C_3$-alkyl, and
$R^{33}$ represents $C_1-C_4$-alkyl,
furthermore
$R^1$ represents the radical

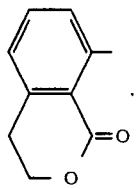

$R^2$ represents hydroxyl or amino, or represents $C_1-C_4$-alkoxy or $C_1-C_4$-alkylamino, each of which is optionally substituted by fluorine, chlorine, methoxy or ethoxy, $R^3$ represents hydrogen, fluorine, chlorine, bromine, $C_1-C_4$-alkyl, $C_1-C_4$-halogenoalkyl, $C_1-C_2$-alkoxy-$C_1-C_2$-alkyl, $C_1-C_4$-alkoxy, $C_1-C_4$-halogenoalkoxy, $C_1-C_4$-alkylthio, $C_1-C_4$-halogenoalkylthio, amino, $C_1-C_4$-alkylamino, dimethylamino or diethylamino, X represents nitrogen or a CH group, Y represents nitrogen or a $CR^4$ group, where $R^4$ represents hydrogen, fluorine, chlorine, bromine, cyano, methyl, formyl, acetyl, methoxycarbonyl or ethoxycarbonyl, and Z represents nitrogen or a —$CR^5$ group, where $R^5$ represents hydrogen, fluorine, chlorine, bromine, $C_1-C_4$-alkyl, $C_1-C_4$-alkoxy, $C_1-C_4$-alkylthio, $C_1-C_4$-alkylamino, dimethylamino or diethylamino, with the exception of N'-(4,6-dimethyl-pyrimidin-2-yl)-N'-(2-methoxycarbonyl-phenylsulphonylamino)-N'''-(2-methoxycarbonyl-phenylsulphonyl)-guanidine.

In particular, the invention relates to compounds of the formula (I) in which
$R^1$ represents the radical

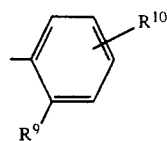

where
$R^9$ represents fluorine, chlorine, bromine, methyl, trifluoromethyl, methoxy, difluoromethoxy, trifluoromethyoxy, $C_1-C_3$-alkylthio, $C_1-C_3$-alkylsulphinyl, $C_1-C_3$-alkylsulphonyl, dimethylaminosulphonyl, diethylaminosulphonyl, N-methoxy-N-methylaminosulphonyl, phenyl, phenoxy or $C_1-C_3$-alkoxycarbonyl, and $R_{10}$ represents hydrogen; furthermore
$R^1$ represents the radical

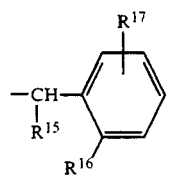

where
$R^{15}$ represents hydrogen, $R^{16}$ represents fluorine, chlorine, bromine, methyl, methoxy, ethoxy, difluoromethoxy, trifluoromethoxy, methoxycarbonyl, ethoxycarbonyl, methylsulphonyl or dimethylaminosulphonyl, and $R^{17}$ represents hydrogen; furthermore
$R^1$ represents the radical

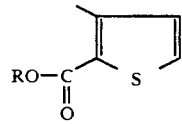

where
R represents methyl or ethyl, or
$R^1$ represents the radical

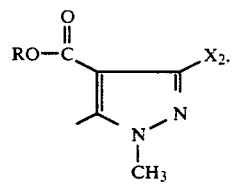

where
R represents methyl or ethyl, and
$X^2$ represents hydrogen or chlorine, $R^2$ represents hydroxyl, amino, methoxy, ethoxy, propoxy, isopropoxy, 2-chloro-ethoxy, 2-methoxy-ethoxy, 2-ethoxy-ethoxy, methylamino, ethylamino, propylamino or isopropylamino, $R^3$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, X represents nitrogen or a —CH group, Y represents nitrogen or a —$CR^4$ group, where $R^4$ represents hydrogen, fluorine, chlorine or methyl, and represents nitrogen or a $-CR^5$ group, where $R^5$ represents nitrogen, fluorine, chlorine, bromine, methyl, ethyl, methoxy, ethoxy, propoxy, isopropoxy, methylthio, ethylthio, methylamino, ethylamino, dimethylamino or diethylamino, with the exception of N'-(4,6-dimethyl-pyrimidin-2-yl)-N'-(2-methoxycarbonyl-phenylsulphonylamino)-N'''-(2-methoxycarbonyl-phenylsulphonyl)-guanidine.

Very particularly preferred are those compounds of the formula (I) in which the group $-COR^2$ is in the ortho-position relative to the $SO_2$ group, and $R^1$, $R^2$, $R^3$, X, Y and Z have the meanings indicated above as being particularly preferred.

If, for example, N'-(4,6-dimethoxy-s-triazin-2-yl)-N'-methoxy-N',N'''-bis-(2-bromo-phenylsulphonyl)guanidine and 2-methoxycarbonyl-benzenesulphonic acid hydrazide are used as the starting substances, the course of the reaction in process (a) according to the invention can be outlined by the following equation:

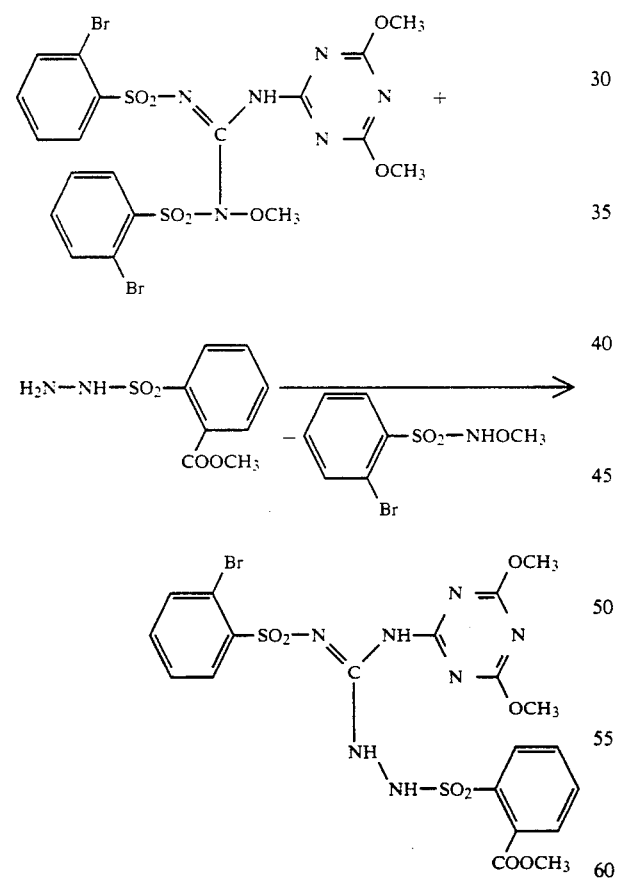

If, for example, N'-(4,6-dimethoxy-pyrimidin-2-yl)-N'-amino-N'''-(2-difluoromethoxy-phenylsulphonyl)-guanidine and 2-ethoxycarbonylbenzenesulphony chloride are used as starting substances, the course of the reaction in process (b) according to the invention can be outlined by the following equation:

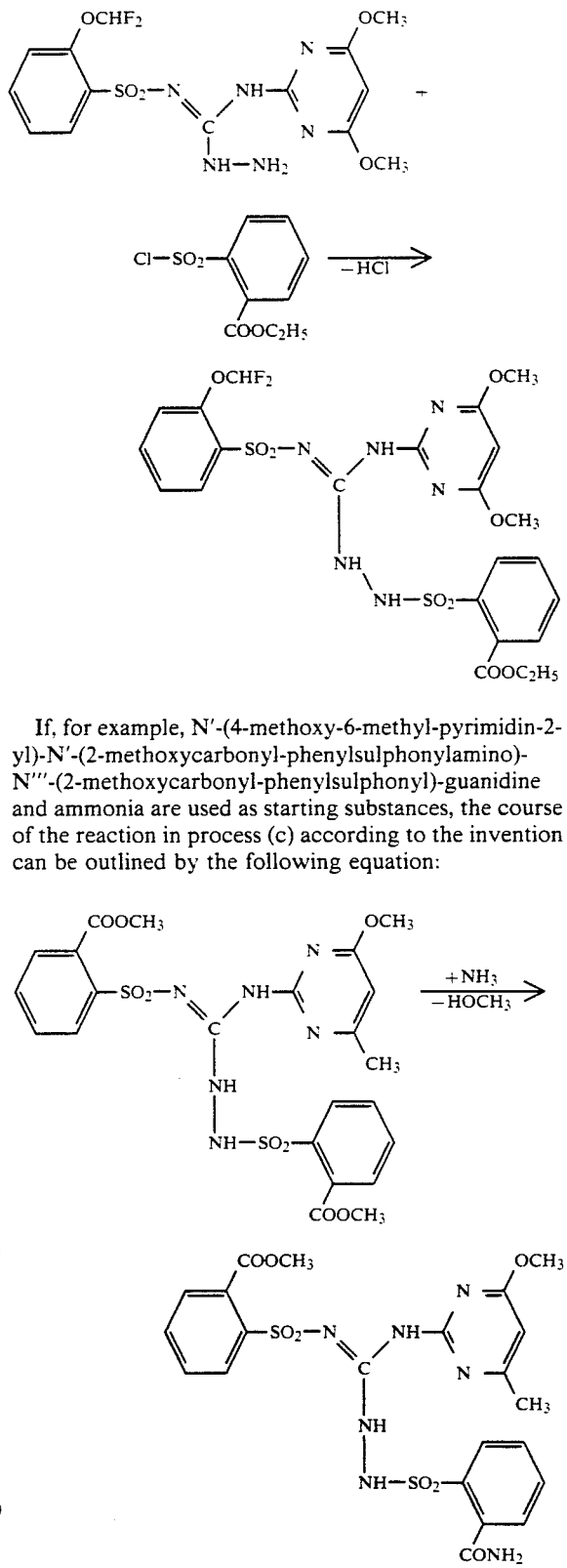

If, for example, N'-(4-methoxy-6-methyl-pyrimidin-2-yl)-N'-(2-methoxycarbonyl-phenylsulphonylamino)-N'''-(2-methoxycarbonyl-phenylsulphonyl)-guanidine and ammonia are used as starting substances, the course of the reaction in process (c) according to the invention can be outlined by the following equation:

Formula (II) provides the general definition of the sulphonyl compounds to be used as the starting substances in process (a) according to the invention. In formula (II), $R^1$, $R^3$, X, Y and Z preferably, or in particular, have those meanings which have already been mentioned above in connection with the description of the compounds of the formula (I) according to the invention as being preferred, or particularly preferred, for $R^1$, $R^3$, X, Y and Z, and A preferably represents one of the leaving groups

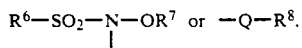

where $R^6$ has the meaning indicated above in the case of $R^1$ as being preferred, but does not have to be identical with $R^1$ in each individual case, $R^7$ represents $C_1$-$C_4$-alkyl, $C_1$-$C_4$-alkenyl or benzyl,
$R^8$ represents $C_1$-$C_4$-alkyl, benzyl or phenyl, and
Q represents oxygen or sulphur.

In particular, A represents the group

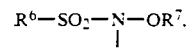

where
$R^6$ has the meaning indicated above in the case of $R^1$ as being particularly preferred, but does not have to be identical with $R^1$ in each individual case, and
$R^7$ represents methyl,
or A represents the group —Q—$R^8$, where
$R^8$ represents methyl or phenyl, and
Q represents oxygen or sulphur.

Examples of the starting substances of the formula (II) are listed in Table 1 below.

TABLE 1

Examples of the starting substances of the formula (II)

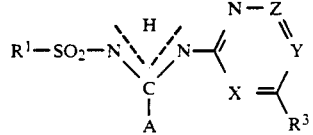

(II)

| A | $R^1$ | $R^3$ | X | Y | Z |
|---|---|---|---|---|---|
| 2-Cl-C₆H₄-SO₂-N(OCH₃)- | 2-Cl-C₆H₄ | CH₃ | N | CH | C—OCH₃ |
| 2-Br-C₆H₄-SO₂-N(OCH₃)- | 2-Br-C₆H₄ | OCH₃ | N | CH | C—OCH₃ |
| 2-F-C₆H₄-SO₂-N(OCH₃)- | 2-F-C₆H₄ | OCH₃ | N | CH | C—OCH₃ |
| 2-CF₃-C₆H₄-SO₂-N(OCH₃)- | 2-CF₃-C₆H₄ | OCH₃ | N | CH | C—OCH₃ |
| 2-OCHF₂-C₆H₄-SO₂-N(OCH₃)- | 2-OCHF₂-C₆H₄ | OCH₃ | N | CH | C—OCH₃ |
| 2-OCF₃-C₆H₄-SO₂-N(OCH₃)- | 2-OCF₃-C₆H₄ | OCH₃ | N | CH | C—OCH₃ |

TABLE 1-continued
Examples of the starting substances of the formula (II)
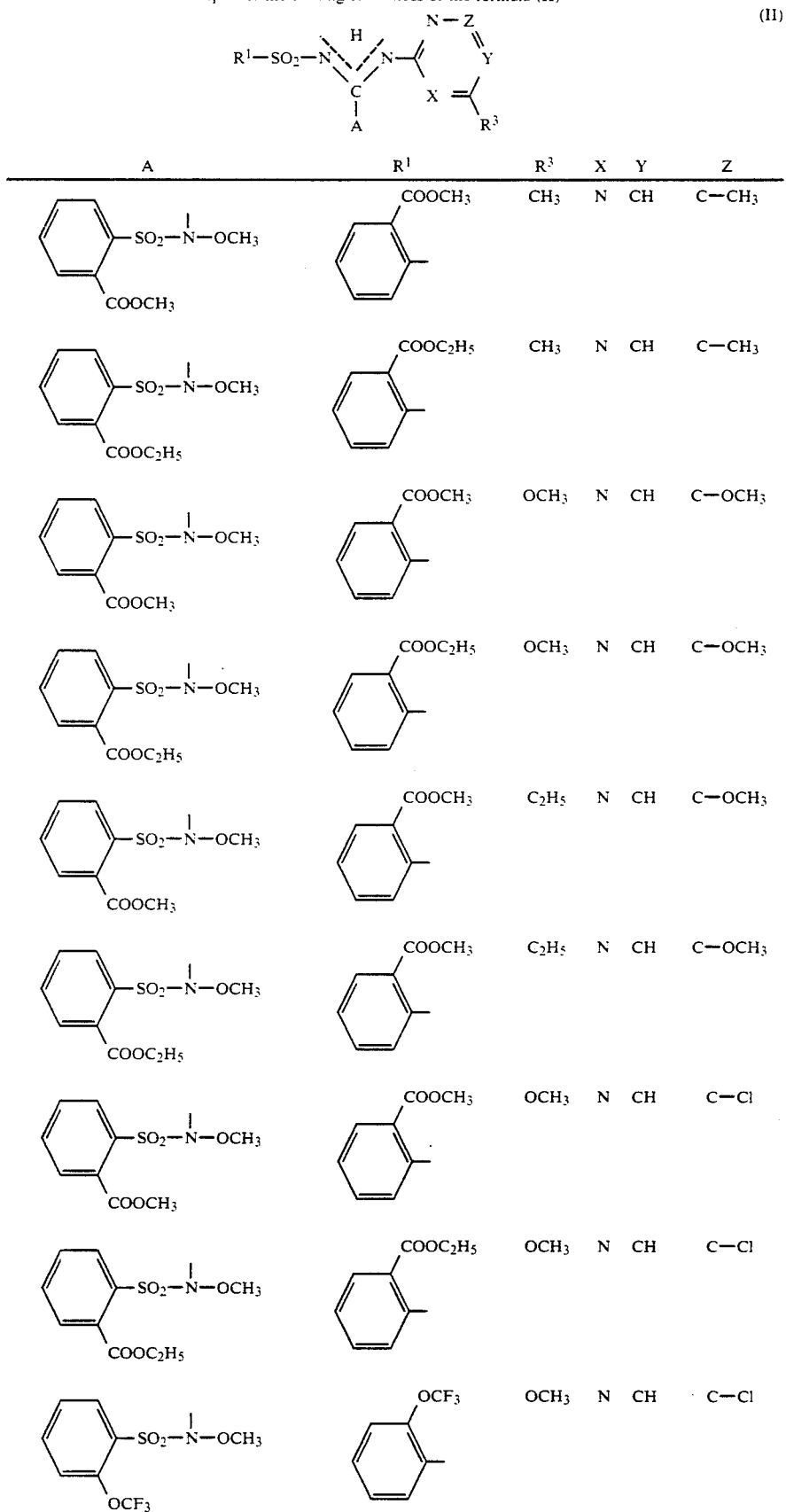

TABLE 1-continued

Examples of the starting substances of the formula (II)

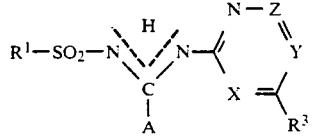

(II)

| A | R$^1$ | R$^3$ | X | Y | Z |
|---|---|---|---|---|---|
| 2-OCHF$_2$-C$_6$H$_4$-SO$_2$-N(OCH$_3$)- | 2-OCHF$_2$-C$_6$H$_4$- | OCH$_3$ | N | CH | C—Cl |
| 2-SO$_2$CH$_3$-C$_6$H$_4$-SO$_2$-N(OCH$_3$)- | 2-SO$_2$CH$_3$-C$_6$H$_4$- | H | N | CH | C—CH$_3$ |
| 2-SO$_2$N(CH$_3$)$_2$-C$_6$H$_4$-SO$_2$-N(OCH$_3$)- | 2-SO$_2$N(CH$_3$)$_2$-C$_6$H$_4$- | CH$_3$ | N | CH | C—OCH$_3$ |
| 2-CH$_3$-C$_6$H$_4$-SO$_2$-N(OCH$_3$)- | 2-CH$_3$-C$_6$H$_4$- | OCH$_3$ | N | CH | C—OCH$_3$ |
| 2-OCH$_3$-C$_6$H$_4$-SO$_2$-N(OCH$_3$)- | 2-OCH$_3$-C$_6$H$_4$- | CH$_3$ | N | CH | C—OCH$_3$ |
| 2-SCH$_3$-C$_6$H$_4$-SO$_2$-N(OCH$_3$)- | 2-SCH$_3$-C$_6$H$_4$- | OCH$_3$ | N | CH | C—OCH$_3$ |
| 2-[SO$_2$N(CH$_3$)(OCH$_3$)]-C$_6$H$_4$-SO$_2$-N(OCH$_3$)- | 2-[SO$_2$N(CH$_3$)(OCH$_3$)]-C$_6$H$_4$- | OCH$_3$ | N | CH | C—OCH$_3$ |
| 2-COOCH$_3$-C$_6$H$_4$-SO$_2$-N(OCH$_3$)- | 2-COOCH$_3$-C$_6$H$_4$- | CH$_3$ | N | CH | C—OC$_2$H$_5$ |
| 2-COOCH$_3$-C$_6$H$_4$-SO$_2$-N(OCH$_3$)- | 2-COOCH$_3$-C$_6$H$_4$- | OCHF$_2$ | N | CH | C—CH$_3$ |

TABLE 1-continued

Examples of the starting substances of the formula (II)

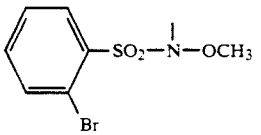

(II)

| A | R¹ | R³ | X | Y | Z |
|---|----|----|---|---|---|
| 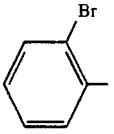 2-Br-C₆H₄-SO₂-N(OCH₃)- | 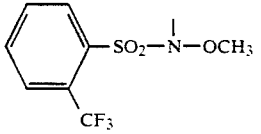 2-Br-C₆H₄- | CH₃ | N | CH | C—SCH₃ |
| 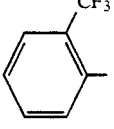 2-CF₃-C₆H₄-SO₂-N(OCH₃)- | 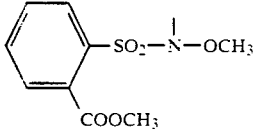 2-CF₃-C₆H₄- | CH₃ | N | CH | C—N(CH₃)₂ |
| 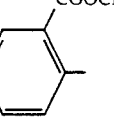 2-COOCH₃-C₆H₄-SO₂-N(OCH₃)- | 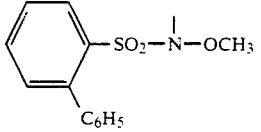 2-COOCH₃-C₆H₄- | OCHF₂ | N | CH | C—OCHF₂ |
| 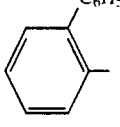 2-C₆H₅-C₆H₄-SO₂-N(OCH₃)- | 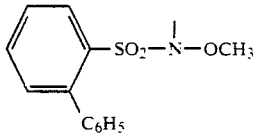 2-C₆H₅-C₆H₄- | OCH₃ | N | CH | C—OCH₃ |
| 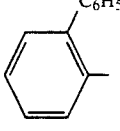 2-C₆H₅-C₆H₄-SO₂-N(OCH₃)- | 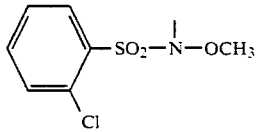 2-C₆H₅-C₆H₄- | OCH₃ | N | N | C—OCH₃ |
| 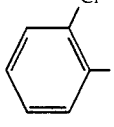 2-Cl-C₆H₄-SO₂-N(OCH₃)- | 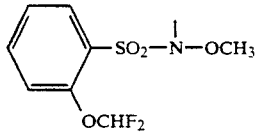 2-Cl-C₆H₄- | CH₃ | N | N | C—OCH₃ |
| 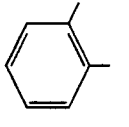 2-OCHF₂-C₆H₄-SO₂-N(OCH₃)- | 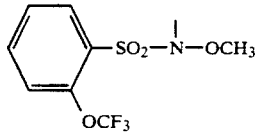 2-OCHF₂-C₆H₄- | OCH₃ | N | N | C—OCH₃ |
| 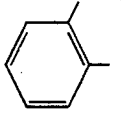 2-OCF₃-C₆H₄-SO₂-N(OCH₃)- | 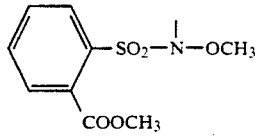 2-OCF₃-C₆H₄- | OCH₃ | N | N | C—OCH₃ |
| 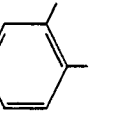 2-COOCH₃-C₆H₄-SO₂-N(OCH₃)- | 2-COOCH₃-C₆H₄- | CH₃ | N | N | C—OCH₃ |

TABLE 1-continued
Examples of the starting substances of the formula (II)
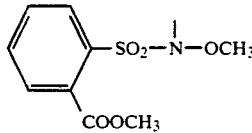
(II)
| A | R¹ | R³ | X | Y | Z |
|---|----|----|---|---|---|
| 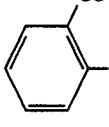 | 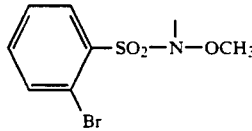 | OCH$_3$ | N | N | C—OCH$_3$ |
| 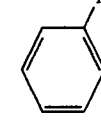 | 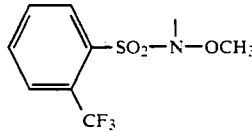 | CH$_3$ | N | N | C—CH$_3$ |
| 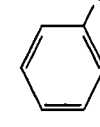 | 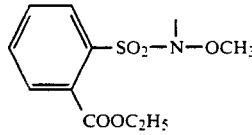 | CH$_3$ | N | N | C—Cl |
| 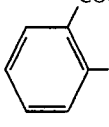 | 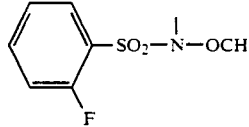 | OCH$_3$ | N | N | C—OCH$_3$ |
| 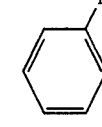 | 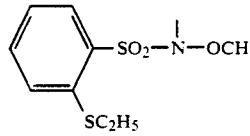 | OCH$_3$ | N | N | C—OCH$_3$ |
| 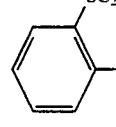 | 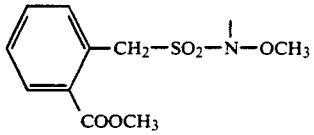 | OCH$_3$ | N | N | C—OCH$_3$ |
| 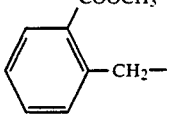 | 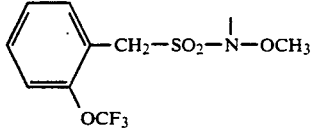 | OCH$_3$ | N | CH | C—OCH$_3$ |
| 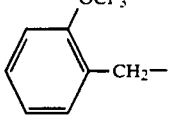 | 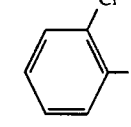 | OCH$_3$ | N | CH | C—OCH$_3$ |
| —OC$_6$H$_5$ |  | CH$_3$ | N | CH | C—CH$_3$ |

TABLE 1-continued

Examples of the starting substances of the formula (II)

$$R^1-SO_2-N\overset{H}{\underset{\underset{A}{C}}{\diagdown}}N-\overset{N-Z}{\underset{X=\underset{R^3}{\diagdown}}{C}}Y \qquad (II)$$

| A | $R^1$ | $R^3$ | X | Y | Z |
|---|---|---|---|---|---|
| —OCH$_3$ | 2-Cl-C$_6$H$_4$ | CH$_3$ | N | CH | C—OCH$_3$ |
| —SCH$_3$ | 2-Cl-C$_6$H$_4$ | OCH$_3$ | N | CH | C—OCH$_3$ |
| —SC$_6$H$_5$ | 2-Cl-C$_6$H$_4$ | OCH$_3$ | N | CH | C—OCH$_3$ |
| 3-(SO$_2$—N(OCH$_3$)—)-2-(COOCH$_3$)-thiophene | 2-(COOCH$_3$)-thiophen-3-yl | CH$_3$ | N | N | C—OCH$_3$ |
| 4-(COOCH$_3$)-5-(SO$_2$—N(OCH$_3$)—)-1-methylpyrazole | 4-(COOCH$_3$)-1-methyl-pyrazol-5-yl | OCH$_3$ | N | CH | C—OCH$_3$ |
| 2-(COOCH$_3$)-C$_6$H$_4$-SO$_2$—N(OCH$_3$)— | 4-(COOC$_2$H$_5$)-1-methyl-pyrazol-5-yl | OCH$_3$ | N | CH | C—OCH$_3$ |

The starting substances of the formula (II) are known and/or can be prepared by processes known per se (cf. EP-A 121,082, EP-A 172,957, EP-A 173,321, EP-A 173,956, EP-A 224,078, EP-A 5,986 and EF-A 24,215).

Formula (III) provides a general definition of the sulphonic acid hydrazides furthermore to be used as starting substances in the process according to the invention. In formula (III), $R^2$ preferably, or in particular, has the meaning which has already been mentioned above in connection with the description of the compounds of the formula (I) according to the invention as being preferred, or particularly preferred, for $R^2$.

Examples of the compounds of the formula (III) which may be mentioned are: 2-methoxycarbonyl-,4-methoxycarbonyl-,2-ethoxycarbonyl- and 4-ethoxycarbonyl-benzenesulphonic acid hydrazide.

The starting substances of the formula (III) are known and/or can be prepared by processes known per se (cf. Org. Synth. 40 (1960), 93-95; EP-A 302,378; Egypt. J. Pharm. Sci 22 (1981), 207-221—cited in Chem. Abstracts 100, 191704y).

Process (a) according to the invention for the preparation of new compounds of the formula (I) is preferably carried out using diluents. Preferred possible diluents for this purpose are water and/or polar organic solvents, such as methanol, ethanol, isopropanol, butanol, isobutanol, sec-butanol, tert-butanol, glycol dimethyl ether, diglycol dimethyl ether, tetrahydrofuran, dioxane, methyl acetate, ethyl acetate, acetonitrile, propionitrile, dimethylformamide, dimethylacetamide, N-methylpyrrolidone, dimethyl sulphoxide and tetramethylene sulphone.

When carrying out process (a) according to the invention, the reaction temperatures can be varied within a substantial range. In general, the process is carried out at temperatures between 0° C. and 150° C., preferably at temperatures between 10° C. and 100° C.

For carrying out process (a) according to the invention, between 1 and 5 moles, preferably between 1 and 3 moles, of sulphonic acid hydrazide of the formula (III) are generally employed per mole of sulphonyl compound of the formula (II).

In general, the reactants are combined at room temperature or with ice-cooling, and the reaction mixture is stirred until the reaction is complete, if appropriate at increased temperature. After cooling, the products of the formula (I) are generally obtained in crystalline form and can be isolated by filtration with suction.

Formula (IV) provides a general definition of the aminoguanidinoazines to be used as the starting substances in process (b) according to the invention for the preparation of compounds of the formula (I).

In formula (IV), $R^1$, $R^3$, X, Y and Z preferably, or in particular, have those meanings which have already been mentioned above in connection with the description of the compounds of the formula (I) according to the invention as being preferred, or particularly preferred, for $R^1$, $R^3$, X, Y and Z.

Examples of the starting substances of the formula (IV) are listed in Table 2 below.

TABLE 2

Examples of the starting substances of the formula (IV)

$$R^1-SO_2-N\underset{\underset{NH-NH_2}{|}}{\overset{H}{\underset{C}{\diagdown}}\!\!\!\diagup}N\!\!-\!\!\underset{R^3}{\overset{N-Z}{\underset{X}{\diagdown}}\!\!\!=\!\!\diagup}Y \quad (IV)$$

| $R^1$ | $R^3$ | X | Y | Z |
|---|---|---|---|---|
| 2-OCF₃-phenyl | OCH₃ | N | CH | C—OCH₃ |
| 2-COOCH₃-phenyl | OCH₃ | N | CH | C—OCH₃ |
| 2-OCHF₂-phenyl | CH₃ | N | CH | C—CH₃ |
| 2-OCF₃-phenyl | CH₃ | N | N | C—OCH₃ |
| 2-OCF₃-phenyl | OCH₃ | N | N | C—OCH₃ |
| 2-Cl-phenyl | CH₃ | N | CH | C—OCH₃ |
| 1-methyl-pyrazol-4-yl (3-COOC₂H₅) | CH₃ | N | CH | C—CH₃ |
| 1-methyl-pyrazol-4-yl (3-COOC₂H₅) | CH₃ | N | N | C—CH₃ |
| 2-Br-phenyl | CH₃ | N | CH | C—CH₃ |
| 2-COOCH₃-phenyl | CH₃ | N | N | C—OCH₃ |
| 2-COOCH₃-phenyl | OCH₃ | N | CH | C—OCH₃ |
| 2-COOC₂H₅-phenyl | CH₃ | N | CH | C—OCH₃ |
| 2-COOC₂H₅-phenyl | OCH₃ | N | CH | C—OCH₃ |
| 2-OCF₃-benzyl | OCH₃ | N | CH | C—OCH₃ |
| 2-F-phenyl | OCH₃ | N | N | C—OCH₃ |

TABLE 2-continued

Examples of the starting substances of the formula (IV)

(IV)

$R^1-SO_2-N\overset{H}{\underset{\underset{NH-NH_2}{C}}{\cdots N}}\overset{N-Z}{\underset{X}{\underset{R^3}{\overset{Y}{\diagdown}}}}$

| $R^1$ | $R^3$ | X | Y | Z |
|---|---|---|---|---|
| 2-OCF$_3$-phenyl | C$_2$H$_5$ | N | CH | C—OCH$_3$ |
| 2-COOC$_2$H$_5$-phenyl | CH$_3$ | N | N | C—OCH$_3$ |
| 2-COOC$_2$H$_5$-phenyl | OCH$_3$ | N | N | C—OCH$_3$ |
| 2-Cl-phenyl | CH$_3$ | N | N | C—OCH$_3$ |
| 2-Cl-phenyl | OCH$_3$ | N | N | C—OCH$_3$ |
| 2-Br-phenyl | OCH$_3$ | N | N | C—OCH$_3$ |
| 2-COOC$_2$H$_5$-phenyl | CH$_3$ | N | CH | C—CH$_3$ |
| 2-CF$_3$-phenyl | CH$_3$ | N | CH | C—CH$_3$ |
| 2-CF$_3$-phenyl | OCH$_3$ | N | CH | C—OCH$_3$ |
| 2-CF$_3$-phenyl | CH$_3$ | N | N | C—OCH$_3$ |
| 2-OCHF$_2$-phenyl | OCH$_3$ | N | CH | C—OCH$_3$ |
| 2-OCHF$_2$-phenyl | OCH$_3$ | N | N | C—OCH$_3$ |
| 2-(OCHF$_2$)-benzyl | OCH$_3$ | N | CH | C—OCH$_3$ |
| 2-(OCHF$_2$)-benzyl | OCH$_3$ | N | N | C—OCH$_3$ |
| 2-COOCH$_3$-phenyl | C$_2$H$_5$ | N | N | C—OCH$_3$ |
| 2-OCF$_3$-phenyl | CH$_3$ | N | CH | C—OC$_2$H$_5$ |
| 2-(COOCH$_3$)-benzyl | OCH$_3$ | N | N | C—OCH$_3$ |
| 4-COOC$_2$H$_5$-5-methyl-1-methylpyrazol-3-yl | OCH$_3$ | N | CH | C—OCH$_3$ |
| 3-methyl-2-COOCH$_3$-thien-2-yl | CH$_3$ | N | N | C—OCH$_3$ |

TABLE 2-continued

Examples of the starting substances of the formula (IV)

$$R^1-SO_2-N\underset{NH-NH_2}{\overset{H}{\underset{C}{\vert}}}N\underset{X}{\overset{N-Z}{\underset{\vert}{\vert}}}Y$$
                                      (IV)

| $R^1$ | $R^3$ | X | Y | Z |
|---|---|---|---|---|
| 2-methyl-thiophene-3-COOCH3 (thiophene with CH3 and COOCH3) | OCH3 | N | N | C—OCH3 |
| 1-methyl-pyrazole-4-COOCH3, 5-CH3 | OCH3 | N | N | C—OCH3 |
| 2-C6H5-phenyl | OCH3 | N | CH | C—OCH3 |
| 2-C6H5-phenyl | OCH3 | N | N | C—OCH3 |
| 2-COOC2H5-phenyl | OCH3 | N | CH | C—Cl |
| 2-CH3-phenyl | CH3 | N | N | C—OCH3 |
| 2-CH3,3-Cl-phenyl | CH3 | N | CH | C—CH3 |
| 2-COOCH3-phenyl | CF3 | N | CH | C—OCH3 |
| 2-COOCH3-phenyl | CH3 | N | CH | C—OCHF2 |
| 2-COOCH3-phenyl | OCH3 | N | CH | C—OCHF2 |
| 2-COOCH3-phenyl | OCHF2 | N | CH | C—OCHF2 |
| 2-COOCH3-phenyl | NHCH3 | N | N | C—OC2H5 |
| 2-COOCH3-phenyl | NHC2H5 | N | N | C—OCH3 |
| 2-COOCH(CH3)2, 4-Cl-phenyl | CH3 | N | N | C—OCH3 |
| 2-COOC2H5, 4-OCHF2-phenyl | OCH3 | N | CH | C—OCH3 |
| 2-OCH2CH2—Cl-phenyl | CH3 | N | N | C—OCH3 |
| 2-OCH2CH2—OCH3-phenyl | OCH3 | N | N | C—OCH3 |
| 2-COOC2H5-phenyl | Cl | N | CH | C—OCH3 |

TABLE 2-continued

Examples of the starting substances of the formula (IV)

$$R^1-SO_2-N\overset{H}{\underset{C}{\diagdown}}\overset{}{\underset{NH-NH_2}{\diagup}}N\overset{}{\underset{X}{\diagdown}}\overset{N-Z}{\underset{R^3}{\diagup}}Y \quad (IV)$$

| $R^1$ | $R^3$ | X | Y | Z |
|---|---|---|---|---|
| 2-(COOCH₃)-phenyl | CH(OCH₃)₂ | N | CH | C—OCH₃ |
| 2-methyl-phenyl-ethyl lactone (isochroman-1-one) | NHCH₃ | N | N | C—OC₂H₅ |
| 2-methyl-3-(CON(CH₃)₂)-pyridyl | OCH₃ | N | CH | C—OCH₃ |
| 2-(OCF₃)-benzyl | OCH₃ | N | N | C—OCH₃ |
| 2-(OCF₃)-benzyl | CH₃ | N | N | C—OCH₃ |
| 2-(OCF₃)-benzyl | CH₃ | N | N | C—CH₃ |
| 2-(OCF₃)-benzyl | NHCH₃ | N | N | C—OC₂H₅ |
| 2-(OCF₃)-benzyl | C₂H₅ | N | N | C—OCH₃ |
| 2-(OCF₃)-benzyl | CH₃ | N | N | C—OC₂H₅ |
| 2-(OCHF₂)-benzyl | CH₃ | N | N | C—OCH₃ |
| 2-(OCHF₂)-benzyl | CH₃ | N | N | C—CH₃ |
| 2-(OCHF₂)-benzyl | NHCH₃ | N | N | C—OC₂H₅ |
| 2-(OCHF₂)-benzyl | C₂H₅ | N | N | C—OCH₃ |
| 2-(OCHF₂)-benzyl | CH₃ | N | N | C—OC₂H₅ |
| 2-(OCF₃)-phenyl | CF₃ | N | CH | C—OCH₃ |
| 3-methyl-2-(COOCH₃)-thienyl | OCHF₂ | N | CH | C—OCHF₂ |
| 2-(COOCH₃)-benzyl | OCH₃ | N | CH | C—OCH₃ |
| 3-Cl-4-(COOCH₃)-5-methyl-1-methyl-pyrazolyl | OCH₃ | N | CH | C—OCH₃ |

The starting substances of the formula (IV) are known and/or can be prepared by processes known per se (cf. EP-A 224,078, U.S. Pat. No. 4,725,303, German Patent Application No. P 3,818,040.5 dated 27.05.1988).

The aminoguanidinoazines of the formula (IV) are obtained when sulphonyl compounds of the general formula (II)—above—are reacted with hydrazine or a hydrazine-water adduct ("hydrazine hydrate") in analogy to process (a) according to the invention, if appropriate in the presence of a diluent, such as, for example, methylene chloride, methanol or ethanol, and if appropriate in the presence of a drying agent, such as, for example, sodium sulphate, at temperatures between $-20°$ C. and $+80°$ C., preferably between $0°$ C. and $50°$ C.

Formula (V) provides a general definition of the sulphonyl halides furthermore to be used as the starting substances in process (b) according to the invention.

In formula (V), $R^2$ preferably, or in particular, has the meaning which has already been mentioned above in connection with the description of the compounds of the formula (I) according to the invention as being preferred, or particularly preferred, for $R^2$, and $X^1$ preferably represents fluorine, chlorine or bromine, in particular chlorine.

The following may be mentioned as examples of the starting substances of the formula (V): 2-methoxycarbonyl-,2-ethoxycarbonyl-,4-methoxycarbonyl- and 4-ethoxycarbonyl-benzenesulphonyl chloride.

The starting substances of the formula (V), as well as the starting compound of the formula (VI), are known and/or can be prepared by processes known per se (cf. EP-A 173,320 and EP-A 173,321).

Process (b) according to the invention for the preparation of the new compounds of the formula (I) is preferably carried out using diluents. Suitable diluents for this purpose are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in process (b) according to the invention are all acid-binding agents which can customarily be used for reactions of this type. The following are preferably suitable: alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate, potassium carbonate, sodium tert-butylate and potassium tert-butylate, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

When carrying out process (b) according to the invention, the reaction temperatures can be varied within a substantial range. In general, the process is carried out at temperatures between $-100°$ C. and $+100°$ C., preferably at temperatures between $-70°$ C. and $+70°$ C.

In general, process (b) according to the invention is carried out under atmospheric pressure. However, it is also possible to carry out the process under increased or reduced pressure.

For carrying out the process (b) according to the invention, the specifically required starting substances are generally employed in approximately equimolar amounts. However, it is also possible to use one of the two specifically employed components in a substantial excess. In general, the reactions are carried out in a suitable diluent, if appropriate in the presence of an acid acceptor, and the reaction mixture is stirred for several hours at the specifically required temperature. In process (b) according to the invention, working-up is carried out in each case by customary methods.

With the proviso that $R^2$ in formula (I) represents optionally substituted alkoxy, formula (I) provides a general definition of the substituted aryl sulphonylaminoguanidinoazines to be used as starting substances in process (c) according to the invention. In this case, $R^1$, $R^3$, X, Y and Z preferably, or in particular, have those meanings which have already been mentioned above in connection with the description of the compounds of the formula (I) according to the invention as being preferred, or particularly preferred, for $R^1$, $R^3$, X, Y and Z, and $R^2$ preferably represents $C_1$-$C_4$-alkoxy which is optionally substituted by fluorine, chlorine, methoxy or ethoxy, in particular $R^2$ represents methoxy, ethoxy, propoxy, isopropoxy, 2-chloro-ethoxy, 2-methoxy-ethoxy or 2-ethoxy-ethoxy.

The compounds of the formula (I) to be employed as the starting substances in process (c) according to the invention are new compounds according to the invention; they can be prepared by process (a) or (b) according to the invention.

Aqueous alkali metal hydroxide solutions which can be employed in process (c) according to the invention are solutions of alkali metal hydroxides, such as, for example, of lithium hydroxide, sodium hydroxide or potassium hydroxide, in water. It is preferred to employ aqueous sodium hydroxide solution in process (c) according to the invention.

Ammonia can be employed in process (c) according to the invention as a gas or in solution, preferably in aqueous solution.

Optionally substituted alkylamines which can be employed in process (c) according to the invention are preferably alkylamines having 1 to 4 carbon atoms which are optionally substituted by fluorine, chlorine, methoxy or ethoxy, in particular methylamine, ethylamine, propylamine and isopropylamine.

If appropriate, process (c) according to the invention is carried out using diluents. Suitable diluents for this purpose are virtually all inert organic solvents, besides water and alcohols, such as, for example, methanol, ethanol and isopropanol. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

When carrying out process (c) according to the invention, the reaction temperatures can be varied within a substantial range. In general, the process is carried out at temperatures between 0° C. and 120° C., preferably at temperatures between 20° C. and 100° C.

In general, process (c) according to the invention is carried out under atmospheric pressure. However, it is also possible to carry out the process under increased or reduced pressure.

For carrying out process (c) according to the invention, between 1 and 10 moles, preferably between 1 and 5 moles, of alkali metal hydroxide, ammonia or amine are generally employed per mole of starting compound of the formula (I).

In general, the starting compound of the formula (I) is first introduced at room temperature into the reaction vessel, if appropriate in a diluent, and the aqueous alkali hydroxide solution, the ammonia or the amine is metered in, if appropriate at increased temperature. The reaction mixture is stirred until the reaction is complete, and working-up is carried out by customary methods (cf. the Preparation Examples).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus und Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf, meadows and pastures, and for the selective combating of weeds in annual cultures.

The compounds of the formula (I) according to the invention are suitable for selectively combating monocotyledon and dicotyledon weeds in monocotyledon and dicotyledon crops, using the pre-emergence method as well as the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2',6'-diethyl-N-methoxymethylacetanilide (ALACHLOR); methyl 6,6-dimethyl-2,4-dioxo-3-[1-(2-propenyloxyamino)-butylidene]-cyclohexanecarboxylate (ALLOXYDIM);2-chloro-4-ethylamino-6-isopropylamino-1,3,5-triazine (ATRAZINE); methyl 2-[[[[[(4,6-dimethoxypyrimidin-2-yl)-amino]-carbonyl]-amino]-sulphonyl]-methyl]-benzoate (BENSULFURON); 3-Bopropyl-2,1,3-benzothiadiazin-4-one-2,2-dioxide(BENTAZONE); methyl 5-(2,4-dichlorophenoxy)-2-nitrobenzoate (BIFENOX); 3,5-dibromo-4-hydroxy-benzonitrile (BROMOXYNIL); N-(butoxymethyl)-2-chloro-N-(2,6-diethylphenyl)-acetamide (BUTACHLOR);ethyl 2-{[(4-chloro-6-methoxy-2-pyrimidinyl)-aminocarbonyl]aminosulphonyl}-benzoate (CHLORIMURON); 2-chloro-N-{[(4-methoxy-6-methyl-1,3,5-triazin-2-yl)-amino]-carbonyl{-benzenesulphonamide (CHLORSULFURON); N,N-dimethyl-N'-(3-chloro-4-methylphenyl)-urea(CHLORTOLURON ;exo-1-methyl-4-(1-methylethyl)-2-(2-methylphenyl-methoxy)-7-oxabicyclo-(2,2,1)-heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); 2-[4-(2,4-dichlorophenoxy)-phenoxy]-propionic acid, its methyl ester or its ethyl ester (DICLOFOP); 2-[(2-chlorophenyl)-methyl]-4,4-dimethylisoxazolidin-3-one (DIMETHAZONE); S-ethyl N,N-di-n-propyl-thiocarbamate (EPTAME); 4-amino-6-t-butyl-3-ethylthio-1,2,4-triazin-5(4H)-one (ETHIOZIN); 2-{4-[(6-chloro-2-benzoxazolyl)oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); N,N-dimethyl-N'-(3-trifluoromethylphenyl)urea (FLUOMETURON); [(4-amino-3,5-dichloro-6-fluoro-2-pyridinyl)-oxy]-acetic acid or its 1-methylheptyl ester (FLUROXYPYR); 5-(2-chloro-4-trifluoromethyl-phenoxy)-N-methylsulphonyl-2-nitrobenzamide (FOMESAFEN); 2-{4-[(3-chloro-5-(trifluoromethyl)-2-pyridinyll-oxy]-phenoxy}propanoic acid or its ethyl ester (HALOXYFOP); 3-cyclohexyl-6-dimethylamino-1-methyl-1,3,5-triazine-2,4-dione (HEXAZINONE); methyl 2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); 3,5-diiodo-4-hydroxybenzonitrile(IOXYNIL);N,N-dimethyl-N'-(4-isopropylphenyl)-urea (ISOPROTURON); 2-ethoxy-1-methyl-2-oxo-ethyl 5-[2-chloro-4-(trifluoromethyl)phenoxy]-2-nitrobenzoate (LACTOFEN); (2-methyl-4-chlorophenoxy)-acetic acid (MCPA); (4-chloro-2-methylphenoxy)propionic acid (MCPP); N-methyl-2-(1,3-benzothiazol-2-yloxy)-acetanilide (MEFENACET);2-chloro-N-(2,6-dimethylphenyl)-N-[(1H)-pyrazol-1-ylmethyl]-acetamide (METAZACHLOR); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); S-ethyi N,N-hexamethylenethiocarbamate (MOLINATE); 1-(3-trifluoromethylphenyl)-4-methylamino-5-chloro-6-pyridazone (NORFLURAZON); 4-(di-n-propylamino)-3,5-dinitrobenzenesulphonamide (ORYZALIN); 2-chloro-4-tri-fluoromethylphenyl 3-ethoxy-4-nitro-phenyl ether (OXYFLUORFEN); N-(1-ethylpropyl)-3,4-dimethyl-2,6-dinitroaniline (PENDIMETHALIN); 0-(6-chloro-3-phenyl-pyridazin 4-yl) S-octyl thiocarbonate (PYRIDATE); ethyl 2-[4-(6-chloro-quinoxalin-2-yl-oxy)-phenoxy]-propionate (QUIZALOFOP-ETHYL); 2-[1-(ethoxamino)-butylidene]-5-(2-ethylthiopropyl)-1,3-cyclohexadione (SETHOXYLIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-[(4-chlorophenyl)methyl]-N,N-diethylthiocarbamate(THIOBENCARB);S-(2,3,3-trichloroallyl) N,N-diisopropylthiocarbamate (TRIALLATE); 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

Preparation Examples

Example 1

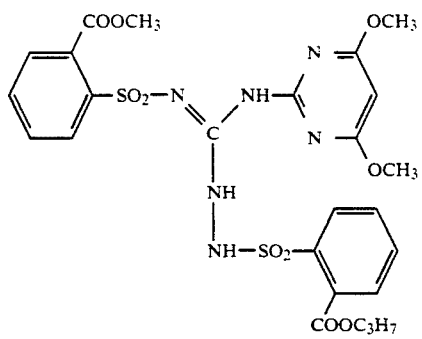

(Process (b))

A mixture of 8.2 g (0.02 mol) of N'-(4,6-dimethoxypyrimidin-2-yl)-N'-amino-N'''-(2-methoxycarbonyl-phenylsulphonyl)-guanidine, 2,5 g (0.022 mol) of diazabicyclo-[2,2,2]-octane (DABCO) and 100 ml of methylene chloride is cooled to −70° C., and a solution of 5.2 g (0.02 mol) of 2-propoxycarbonyl-benzenesulphonyl chloride in 20 ml of methylene chloride is added dropwise to this mixture with stirring. After the cooling bath has been removed, the reaction mixture is stirred for 12 hours, diluted with 100 ml of methylene chloride and shaken with 50 ml of 1N-hydrochloric acid. The product which is obtained in crystalline form during this process is isolated by filtration with suction.

This gives 7.9 g (62% of theory) of N'-(4,6-dimethoxypyrimidin-2-yl)-N'-(2-propoxycarbonyl-phenylsulphonylamino)-N''''-(2-methoxycarbonyl-phenylsulphonyl)guanidine of melting point 180° C.

Example 2

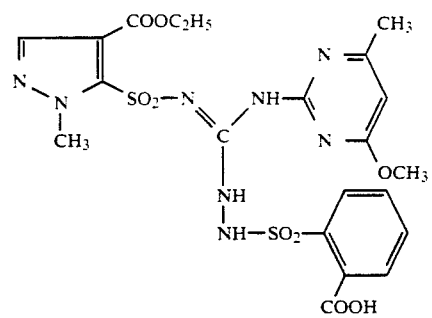

(Process (b))

4.6 g (0.025 mol) of sulphobenzoic anhydride are added to a stirred mixture of 10.3 g (0.025 mol) of N'-(4-methoxy-6-methyl-pyrimidin-2-yl)-N'-amino-N'''-(1-methyl-4-ethoxycarbonyl-pyrazol-5-yl-sulphonyl)-guanidine and 100 ml of acetonitrile, and the reaction mixture is stirred for a further 3 hours at 20° C. The product which is obtained in crystalline form during this process is then isolated by filtration with suction.

This gives 5.0 g (34% of theory) of N'-(4-methoxy-6-methyl-pyrimidin-2-yl)-N'-(2-carboxy-phenylsulphonylamino)-N'''-(1-methyl-4-ethoxycarbonylpyrazol-5-yl-sulphonyl)-guanidine of melting point 228° C., with decomposition.

For example, the compounds of the formula (I) listed in Table 3 below can also be prepared analogously to Examples 1 and 2 and following the general description of the preparation processes according to the invention.

TABLE 3

Examples of the compounds of the formula (I)$_{f)}$

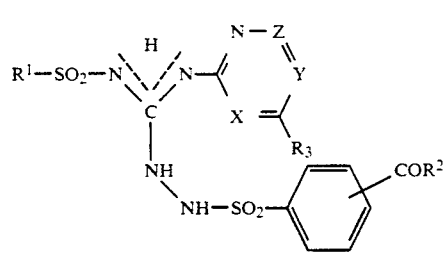

| Example No. | R$^1$ | Position —COR$^2$ | R$^3$ | X | Y | Z | Melting point = M.p. (°C.) |
|---|---|---|---|---|---|---|---|
| 3 | ![pyrazole with COOC$_2$H$_5$, N-N-CH$_3$] | (2-)COOCH$_3$ | CH$_3$ | N | CH | C—CH$_3$ | 157 |
| 4 | ![pyrazole with COOC$_2$H$_5$, N-N-CH$_3$] | (2-)COOCH$_3$ | CH$_3$ | N | CH | C—OCH$_3$ | 143 |

TABLE 3-continued

Examples of the compounds of the formula (I)$_f$)

$$R^1-SO_2-N \overset{H}{\underset{C}{\big|}} \overset{N}{\underset{NH}{\big/}} C \overset{N-Z}{\underset{X}{\big/}} \overset{}{\underset{R_3}{\big|}} Y \qquad (I)$$

$$NH-SO_2-\underset{COR^2}{\bigcirc}$$

| Example No. | R$^1$ | Position —COR$^2$ | R$^3$ | X | Y | Z | Melting point = M.p. (°C.) |
|---|---|---|---|---|---|---|---|
| 5 | [pyrazole-COOC$_2$H$_5$, N-CH$_3$] | (2-)COOCH$_3$ | OCH$_3$ | N | CH | C—OCH$_3$ | 177 |
| 6 | [pyrazole-COOC$_2$H$_5$, N-CH$_3$] | (2-)COOC$_2$H$_5$ | CH$_3$ | N | CH | C—OCH$_3$ | 167 |
| 7 | [pyrazole-COOC$_2$H$_5$, N-CH$_3$] | (2-)COOC$_2$H$_5$ | OCH$_3$ | N | CH | C—OCH$_3$ | 167 |
| 8 | [pyrazole-COOC$_2$H$_5$, N-CH$_3$] | (2-)COOC$_2$H$_5$ | CH$_3$ | N | CH | C—CH$_3$ | 163 |
| 9 | [thiophene-COOCH$_3$] | (2-)COOCH$_3$ | CH$_3$ | N | CH | C—CH$_3$ | 199 |
| 10 | [thiophene-COOCH$_3$] | (2-)COOCH$_3$ | OCH$_3$ | N | CH | C—OCH$_3$ | 193 |
| 11 | [phenyl-COOCH$_3$] | (2-)COOC$_3$H$_7$-iso | CH$_3$ | N | CH | C—CH$_3$ | 159 |
| 12 | [phenyl-COOCH$_3$] | (2-)COOC$_2$H$_5$ | CH$_3$ | N | CH | C—CH$_3$ | 199 |
| 13 | [phenyl-COOCH$_3$] | (2-)COOC$_3$H$_7$-n | CH$_3$ | N | CH | C—CH$_3$ | 161 |

TABLE 3-continued

Examples of the compounds of the formula (I)$_{I_1}$

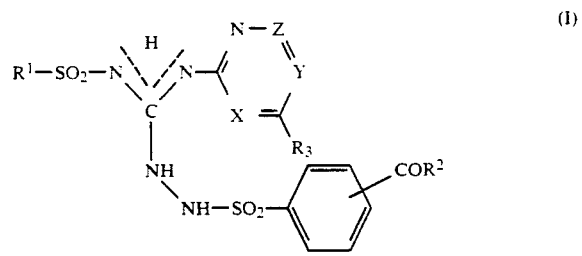

(I)

| Example No. | R$^1$ | Position —COR$^2$ | R$^3$ | X | Y | Z | Melting point = M.p. (°C.) |
|---|---|---|---|---|---|---|---|
| 14 | 2-COOCH$_3$-C$_6$H$_4$ | (2-)COOCH$_2$CH$_2$Cl | CH$_3$ | N | CH | C—CH$_3$ | 158 |
| 15 | 2-COOCH$_3$-C$_6$H$_4$ | (2-)COOCH$_2$CH$_2$OC$_2$H$_5$ | CH$_3$ | N | CH | C—CH$_3$ | 100 |
| 16 | 2-COOCH$_3$-C$_6$H$_4$ | (2-)COOCH$_2$CH$_2$OC$_2$H$_5$ | OCH$_3$ | N | CH | C—OCH$_3$ | 194 |
| 17 | 2-COOCH$_3$-C$_6$H$_4$ | (2-)COOC$_3$H$_7$-iso | OCH$_3$ | N | CH | C—OCH$_3$ | 192 |
| 18 | 2-COOCH$_3$-C$_6$H$_4$ | (2-)COOCH$_2$CH$_2$Cl | OCH$_3$ | N | CH | C—OCH$_3$ | 206 |
| 19 | 2-COOCH$_3$-C$_6$H$_4$ | (2-)COOH | CH$_3$ | N | CH | C—CH$_3$ | 208 |
| 20 | 2-C$_6$H$_5$-C$_6$H$_4$ | (2-)COOCH$_3$ | OCH$_3$ | N | N | C—OCH$_3$ | 172 |
| 21 | 2-C$_6$H$_5$-C$_6$H$_4$ | (2-)COOCH$_3$ | CH$_3$ | N | CH | C—CH$_3$ | 142 |
| 22 | 2-C$_6$H$_5$-C$_6$H$_4$ | (2-)COOCH$_3$ | OCH$_3$ | N | CH | C—OCH$_3$ | 187 |

TABLE 3-continued

Examples of the compounds of the formula (I)$_{j_1}$

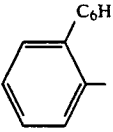

(I)

| Example No | R$^1$ | Position —COR$^2$ | R$^3$ | X | Y | Z | Melting point = M.p. (°C.) |
|---|---|---|---|---|---|---|---|
| 23 | 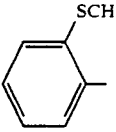 C$_6$H$_5$ | (2-)COOCH$_3$ | CH$_3$ | N | N | C—OCH$_3$ | 139 |
| 24 | 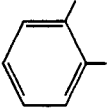 SCH$_3$ | (2-)COOCH$_3$ | CH$_3$ | N | CH | C—CH$_3$ | 177 |
| 25 | 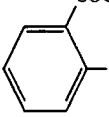 SCH$_3$ | (2-)COOCH$_3$ | OCH$_3$ | N | CH | C—OCH$_3$ | 143 |
| 26 | 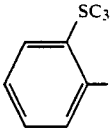 SOCH$_3$ | (2-)COOCH$_3$ | OCH$_3$ | N | CH | C—OCH$_3$ | 194 |
| 27 | 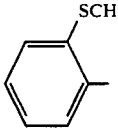 SC$_3$H$_7$-iso | (2-)COOCH$_3$ | OCH$_3$ | N | CH | C—OCH$_3$ | 142 |
| 28 | 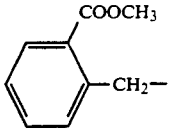 SCH$_3$ | (2-)COOCH$_3$ | OCH$_3$ | N | N | C—OCH$_3$ | 173 |
| 29 | 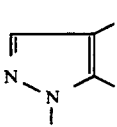 COOCH$_3$ —CH$_2$— | (2-)COOCH$_3$ | OCH$_3$ | N | CH | C—OCH$_3$ | 175 |
| 30 | 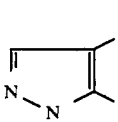 COOC$_2$H$_5$ | (2)-COOC$_3$H$_7$-i | CH$_3$ | N | CH | C—CH$_3$ | 141 |
| 31 | 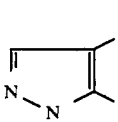 COOC$_2$H$_5$ | (2)-COOC$_3$H$_7$-i | OCH$_3$ | N | CH | C—CH$_3$ | 159 |

TABLE 3-continued

Examples of the compounds of the formula (I)

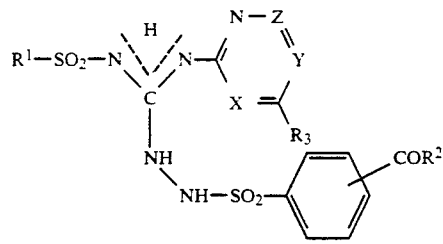

| Example No. | R¹ | Position —COR² | R³ | X | Y | Z | Melting point = M.p. (°C.) |
|---|---|---|---|---|---|---|---|
| 32 | pyrazole with COOC₂H₅, CH₃ groups, N-CH₃ | (2)-COOC₃H₇-i | OCH₃ | N | CH | C—OCH₃ | 172 |
| 33 | phenyl with COOCH₃ | (2)-CONHCH(CH₃)₂ | CH₃ | N | CH | C—CH₃ | 220 |
| 34 | pyrazole with COOC₂H₅, CH₃ groups, N-C₆H₅ | (2)-COOCH₃ | OCH₃ | N | CH | C—CH₃ | 186 |
| 35 | pyrazole with COOC₂H₅, CH₃ groups, N-C₆H₅ | (2)-COOC₂H₅ | CH₃ | N | CH | C—CH₃ | 149 |
| 36 | pyrazole with COOC₂H₅, CH₃ groups, N-C₆H₅ | (2)-COOC₂H₅ | OCH₃ | N | CH | C—OCH₃ | 176 |
| 37 | pyrazole with COOC₂H₅, CH₃ groups, N-C₆H₅ | (2)-COOCH(CH₃)₂ | OCH₃ | N | CH | C—OCH₃ | 165 |
| 38 | pyrazole with COOC₂H₅, CH₃ groups, N-C₆H₅ | (2)-COOCH₃ | OCH₃ | N | CH | C—CH₃ | 166 |
| 39 | pyrazole with COOC₂H₅, CH₃ groups, N-C₆H₅ | (2)-COOCH₃ | OCH₃ | N | CH | C—CH₃ | 178 |

TABLE 3-continued

Examples of the compounds of the formula (I)$_{f)}$ $$R^1-SO_2-N\overset{H}{\underset{C}{\diagdown}}\overset{}{\underset{}{\diagup}}N\overset{}{\underset{}{\diagdown}}C\overset{N-Z}{\underset{X}{\diagup}}\overset{}{\underset{R_3}{\diagdown}}Y$$

with NH—NH—SO$_2$ linked to phenyl bearing COR$^2$ (I)

| Example No. | R$^1$ | Position —COR$^2$ | R$^3$ | X | Y | Z | Melting point = M.p. (°C.) |
|---|---|---|---|---|---|---|---|
| 40 | 4-COOC$_2$H$_5$, 3-CH$_3$, 1-C$_6$H$_5$-pyrazol-5-yl | (2)-COOCH(CH$_3$)$_2$ | OCH$_3$ | N | CH | C—CH$_3$ | 152 |
| 41 | 4-COOC$_2$H$_5$, 3-CH$_3$, 1-CH$_3$-pyrazol-5-yl | (2)-COOCH$_3$ | CH$_3$ | N | CH | CH | 161 |
| 42 | 4-COOC$_2$H$_5$, 3-CH$_3$, 1-CH$_3$-pyrazol-5-yl | (2)-COOC$_4$H$_9$-n | OCH$_3$ | N | CH | C—CH$_3$ | 141 |
| 43 | 4-COOC$_2$H$_5$, 3-CH$_3$, 1-CH$_3$-pyrazol-5-yl | (2)-COOC$_4$H$_9$-s | OCH$_3$ | N | CH | C—CH$_3$ | 158 |
| 44 | 4-COOC$_2$H$_5$, 3-CH$_3$, 1-CH$_3$-pyrazol-5-yl | (2)-COOC$_4$H$_9$-s | OCH$_3$ | N | CH | C—OCH$_3$ | 122 |
| 45 | 4-COOC$_2$H$_5$, 3-CH$_3$, 1-CH$_3$-pyrazol-5-yl | (2)-COOC$_4$H$_9$-n | CH$_3$ | N | CH | C—CH$_3$ | 132 |
| 46 | 4-COOC$_2$H$_5$, 3-CH$_3$, 1-CH$_3$-pyrazol-5-yl | (2)-COOC$_4$H$_9$-n | OCH$_3$ | N | CH | C—OCH$_3$ | 153 |
| 47 | 4-COOC$_2$H$_5$, 3-CH$_3$, 1-C$_6$H$_5$-pyrazol-5-yl | (2)-COOC$_4$H$_9$-s | OCH$_3$ | N | CH | C—CH$_3$ | 154 |

TABLE 3-continued

Examples of the compounds of the formula (I)

$$R^1-SO_2-N \underset{NH}{\overset{H}{\underset{\|}{C}}} N \underset{NH-SO_2}{\overset{N-Z}{\underset{X}{\bigvee}}} \underset{R_3}{\overset{Y}{\bigvee}} COR^2 \quad (I)$$

| Example No. | R¹ | Position —COR² | R³ | X | Y | Z | Melting point = M.p. (°C.) |
|---|---|---|---|---|---|---|---|
| 48 | 4-COOC₂H₅, 3-CH₃, 1-CH₃-pyrazol-5-yl | (2)-COOC₄H₉-s | CH₃ | N | CH | C—CH₃ | 121 |
| 49 | 4-COOC₂H₅, 3-CH₃, 1-CH(CH₃)₂-pyrazol-5-yl | (2)-COOCH₃ | OCH₃ | N | CH | C—OCH₃ | 170 |
| 50 | 4-COOC₂H₅, 3-CH₃, 1-CH(CH₃)₂-pyrazol-5-yl | (2)-COOC₂H₅ | OCH₃ | N | CH | C—OCH₃ | 188 |
| 51 | 4-COOC₂H₅, 3-CH₃, 1-C₆H₅-pyrazol-5-yl | (2)-COOC₄H₉-n | CH₃ | N | CH | C—CH₃ | 142 |
| 52 | 4-COOC₂H₅, 3-CH₃, 1-CH₃-pyrazol-5-yl | (2)-COOC₃H₇-n | OCH₃ | N | CH | C—CH₃ | 148 |
| 53 | 4-COOC₂H₅, 3-CH₃, 1-C₆H₅-pyrazol-5-yl | (2)-COOC₄H₉-n | OCH₃ | N | CH | C—OCH₃ | 180 |
| 54 | 4-COOC₂H₅, 3-CH₃, 1-CH₃-pyrazol-5-yl | (2)-COOC₃H₇-n | CH₃ | N | CH | C—CH₃ | 126 |
| 55 | 4-COOC₂H₅, 3-CH₃, 1-CH₃-pyrazol-5-yl | (2)-COOC₃H₇-n | OCH₃ | N | CH | C—OCH₃ | 162 |

TABLE 3-continued

Examples of the compounds of the formula (I)*f*)

$$R^1-SO_2-N\underset{NH}{\overset{H}{\underset{\underset{NH-SO_2}{|}}{\overset{|}{C}}}}N\underset{X}{\overset{N-Z}{\underset{\|}{\rightleftharpoons}}}Y \quad (I)$$

(with phenyl ring bearing $R_3$ and $COR^2$)

| Example No. | R¹ | Position —COR² | R³ | X | Y | Z | Melting point = M.p. (°C.) |
|---|---|---|---|---|---|---|---|
| 56 | 4-COOC₂H₅, 3-CH₃, 1-C₆H₅-pyrazol-5-yl | (2)-COOC₄H₉-n | OCH₃ | N | CH | C—CH₃ | 107 |
| 57 | 4-COOC₂H₅, 3-CH₃, 1-C₆H₅-pyrazol-5-yl | (2)-COOC₃H₇-n | OCH₃ | N | CH | C—CH₃ | 182 |
| 58 | 4-COOC₂H₅, 3-CH₃, 1-C₆H₅-pyrazol-5-yl | (2)-COOCH(CH₃)₂ | OCH₃ | N | CH | C—CH₃ | 142 |
| 59 | 2,6-dichlorobenzyl | (2)-COOCH₃ | OCH₃ | N | CH | C—CH₃ | 191 |
| 60 | 2-SO₂N(CH₃)₂-phenyl | (2)-COOCH₃ | OCH₃ | N | CH | C—CH₃ | 192 |
| 61 | 2-SO₂N(CH₃)(OCH₃)-phenyl | (2)-COOCH₃ | OCH₃ | N | CH | C—CH₃ | 142 |
| 62 | 2-SO₂N(CH₃)₂-phenyl | (2)-COOCH₃ | CH₃ | N | CH | CH | 178 |
| 63 | 2-SO₂N(CH₃)(OCH₃)-phenyl | (2)-COOCH₃ | CH₃ | N | CH | CH | 184 |

TABLE 3-continued

Examples of the compounds of the formula (I)$_{j}$

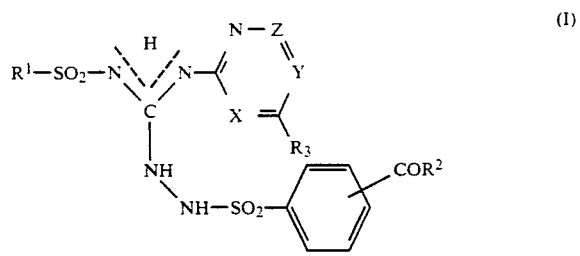

| Example No. | R$^1$ | Position —COR$^2$ | R$^3$ | X | Y | Z | Melting point = M.p. (°C.) |
|---|---|---|---|---|---|---|---|
| 64 | SO$_2$N(CH$_3$)$_2$ (phenyl) | (2)-COOC$_2$H$_5$ | CH$_3$ | N | CH | CH | 168 |
| 65 | SO$_2$N(CH$_3$)$_2$ (phenyl) | (2)-COOC$_3$H$_7$-n | CH$_3$ | N | CH | CH | 163 |
| 66 | SO$_2$N(CH$_3$)$_2$ (phenyl) | (2)-COOCH(CH$_3$)$_2$ | CH$_3$ | N | CH | CH | 166 |
| 67 | SO$_2$N(CH$_3$)$_2$ (phenyl) | (2)-COOC$_4$H$_9$-n | CH$_3$ | N | CH | CH | 165 |
| 68 | OCF$_3$ (phenyl) | (2)-COOCH$_3$ | OCH$_3$ | N | CH | C—CH$_3$ | 184 |
| 69 | CF$_3$ (phenyl) | (2)-COOCH$_3$ | OCH$_3$ | N | CH | C—OCH$_3$ | 189 |
| 70 | COOCH$_3$ (phenyl) | (2)-CONHCH$_2$CH$_2$OCH$_3$ | CH$_3$ | N | CH | C—CH$_3$ | 184 |
| 71 | COOCH$_3$ (phenyl) | (2)-CONH(CH$_2$)$_3$OCH$_3$ | CH$_3$ | N | CH | C—CH$_3$ | 166 |
| 72 | C$_6$H$_5$ (phenyl) | (2)-COOCH$_3$ | OCH$_3$ | N | CH | C—CH$_3$ | 107 |

TABLE 3-continued

Examples of the compounds of the formula (I)$_f$

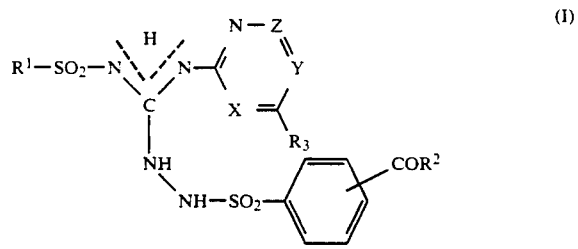

| Example No. | R$^1$ | Position —COR$^2$ | R$^3$ | X | Y | Z | Melting point = M.p. (°C.) |
|---|---|---|---|---|---|---|---|
| 73 | COOCH(CH$_3$)$_2$-phenyl | (2)-COOCH$_3$ | OCH$_3$ | N | N | C—OCH$_3$ | 115 |
| 74 | COOCH(CH$_3$)$_2$-phenyl | (2)-COOCH$_3$ | OCH$_3$ | N | CH | C—OCH$_3$ | 164 |
| 75 | COOCH(CH$_3$)$_2$-phenyl | (2)-COOCH$_3$ | CH$_3$ | N | CH | C—CH$_3$ | 159 |

The preparation of the compound listed in Table 3 as Example No. 19 is described in detail below:

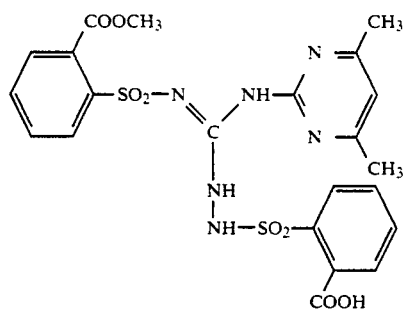

(Process (c))

3.0 g (5.0 mmol) of N'-(4,6-dimethyl-pyrimidin-2-yl)-N',-(2-(2-chloro-ethoxycarbonyl)-phenylsulphonylamino)-N'''-(2-methoxycarbonyl-phenylsulphonyl)-guanidine are suspended in 20 ml of water, and 50% strength sodium hydroxide solution is added dropwise at: 60° C. to this suspension, during which process a pH higher than 12 should be avoided. After cooling, the clear solution which has formed is shaken three times with 50 ml portions of chloroform; the aqueous phase is then filtered and a pH of 5 is established by adding concentrated sulphuric acid. The solid which has precipitated is filtered off, washed with water and taken up in methylene chloride, and the mixture is dried over sodium sulphate and filtered. The solvent is carefully removed from the filtrate by distillation under a water pump vacuum.

This gives 1.0 g (33% of theory) of N'-(4,6-dimethyl-pyrimidin-2-yl)-N'-(2-carboxy-phenylsulphonylamino)-N'''-(2-methoxycarbonyl-phenylsulphonyl)-guanidine of melting point 208° C.

The preparation of the compound listed in Table 3 as Example No. 33 is described in detail below:

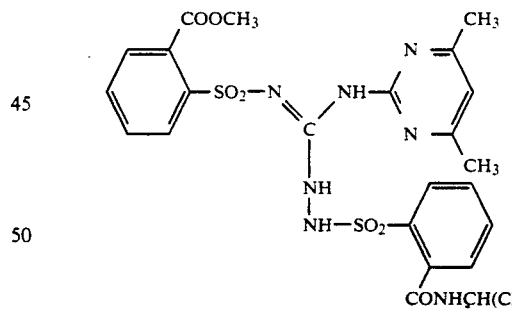

(Process (c))

A mixture of 3.0 g (5.0 mmol) of N'-(4,6-dimethyl-pyrimidin-2-yl)-N'-(2-(2-chloro-ethoxycarbonyl)-phenylsulphonylamino)-N'''-(2-methoxycarbonyl-phenylsulphonyl)-guanidine, 1,5 g (25 mmol) of iso-propylamine and ml of tetrahydrofuran is stirred for 24 hours at 60° C. and then concentrated. The residue is brought to crystallization by trituration with methanol, and the product is isolated by filtration with suction.

This gives 1.5 g (50% of theory) of N'-(4,6-dimethyl-pyrimidin-2-yl)-N'-(2-isopropylaminocarbonylphenyl-sulphonylamino)-N'''-(2-methoxycarbonyl-phenylsulphonyl)-guanidine of melting point 220° C.

Starting substances of the formula (IV)

Example (IV-1)

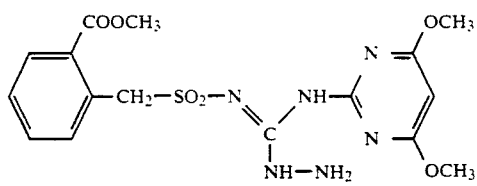

1.3 g (0.025 mol) of hydrazine hydrate are added at an initial temperature of 20° C. to a stirred suspension of 15.9 g (0.025 mol) of N'-(4,6-dimethoxy-pyrimidin-2-yl)-N'-methoxy-N'-(2-methoxycarbonyl-phenylsulphonyl)N'''-(2-methoxycarbonyl-benzylsulphonyl)-guanidine in 100 ml of methanol, during which process the temperature of the reaction mixture rises to 30° C. and a clear solution is formed. The mixture is stirred for 4 hours at 20° C. to 30° C., and the product which is then separated in crystalline form is isolated by filtration with suction.

This gives 9.5 g (89% of theory) of N'-(4,6-dimethoxypyrimidin-2-yl)-N'-amino-N'''-(2-methoxycarbonyl-benzylsulphonyl)-guanidine of melting point 166° C.

Use Examples

In the Use Examples which follow, the compounds listed below are used as comparison substances:

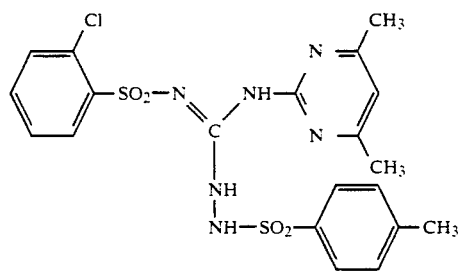
(A)

N'-(4,6-dimethyl-pyrimidin-2-yl)-N'-(4-methyl-phenylsulphonylamino)-N''''-(2-chloro-phenylsulphonyl)guanidine (disclosed in EP-A 121,082).

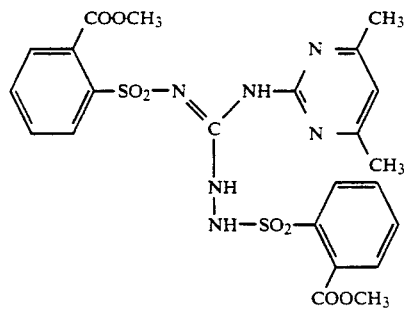
(B)

N'-(4,6-dimethyl-pyrimidin-2-yl)-N'-(2-methoxycarbonylphenylsulphonylamino)-N''''-(2-methoxycarbonylphenylsulphonyl)-guanidine (disclosed in EP-A 302,378).

Example A

Post-emergence test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, a markedly better selectivity towards crop plants, compared with the prior art, is shown for example by the compounds of Preparation Examples (1), (4), (5), (7), (10), (17), (18), (19), (25), (26), (29) and (67).

Example B

Pre-emergence test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. It is expedient here to keep constant the amount of water per unit area. The concentration of active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a markedly better selectivity towards crop plants, compared with the prior art, is shown for example by the compounds of Preparation Examples (4), (5), (7), (10), (18), (19), (25), (26) and (67).

It will be appreciated that the instant specification is set forth by way of illustration and not limitation, and that various modifications and changes may be made without departing from the spirit and scope of the present invention.

What is claimed is:

1. A substituted arylsulphonylaminoguanidinoazine of the formula

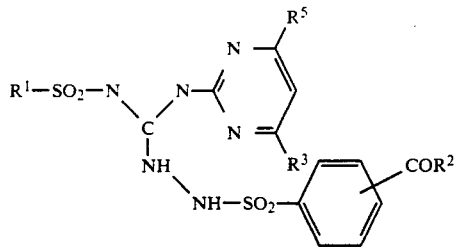

in which represents the radical

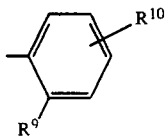

where

R² represents fluorine, chlorine, bromine, methyl, trifluoromethyl, methoxy, difluoromethoxy, trifluoromethoxy, C₁-C₃-alkylthio, C_a-C₃-alkylsulphinyl, C₁-C₃-alkylsulphonyl, dimethylaminosulphonyl diethylaminosulphonyl, N-methoxy-N-methylaminosulphonyl, phenyl, phenoxy or C₁-C₃-alkoxycarbonyl, and R₁₀ represents hydrogen; or furthermore R¹ represents the radical

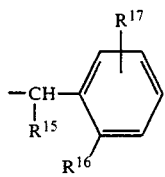

where

R¹⁵ represents hydrogen,

R¹⁶ represents fluorine, chlorine, bromine, methyl, methoxy, ethoxy, difluoromethoxy, trifluoromethoxy, methoxycarbonyl, ethoxycarbonyl, methylsulphonyl or dimethylaminosulphonyl, and R¹⁷ represents hydrogen; or furthermore R¹ represents the radical

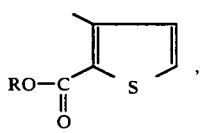

where

R represents methyl or ethyl, or

R¹ represents the radical

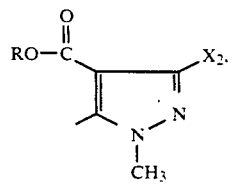

where

R represents methyl or ethyl, and

X² represents hydrogen or chlorine,

R² represents hydroxyl, amino, methoxy, ethoxy, propoxy, isopropoxy, 2-chloro-ethoxy, 2-methoxyethoxy, 2-ethoxy-ethoxy, methylamino, ethylamino, propylamino or isopropylamino, R³ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, and p1 R⁵ represents hydrogen, fluorine, chlorine, bromine, methoxy, ethoxy, propoxy, isopropoxy, methylthio, ethylthio, methylamino, ethylamino, dimethylamino or diethylamino.

2. A compound according to claim 1, in which the group —COR² is in the ortho-position relative to the SO₂ group.

3. A compound according to claim 1, wherein such compound is N'-(4-methoxy-6-methyl-pyrimidin-2-yl)-N'-(2-methoxycarbonyl-phenylsulphonylamino)-N'''-(1-methyl-4-ethoxycarbonylpyrazol-5-yl-sulphonyl)-guanidine of the formula

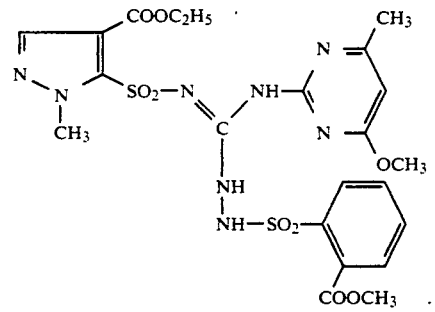

4. A compound according to claim 1, wherein such compound is N'-(4,6-dimethoxy-pyrimidin-2-yl)-N'-(2-ethoxycarbonyl-phenylsulphonylamino)-N'''-(1-methy-4-ethoxycarbonylpyrazol-5-yl-sulphonyl)guanidine of the formula

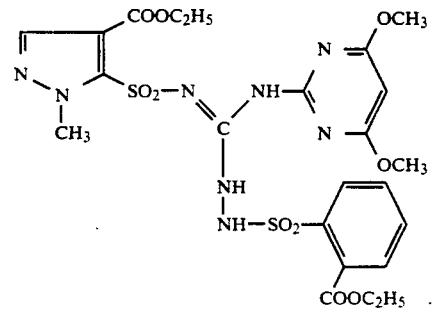

5. A compound according to claim 1, wherein such compound is N'-(4,6-dimethoxy-pyrimidin-2-yl)-N'-(2- methoxycarbonyl-phenylsulphonylamino)-N'''-(2-methylmercaptophenylsulphonyl)-guanidine of the formula

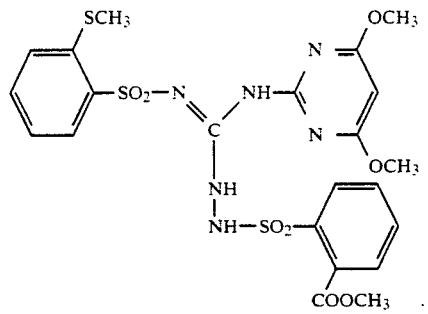

6. A compound according to claim 1, wherein such compound is N'-(4,6-dimethoxy-pyrimidin-2-yl)-N'-(2-methoxycarbonyl-phenylsulphonylamino)-N'''-(2-methylsulfinylphenylsulphonyl)-guanidine of the formula

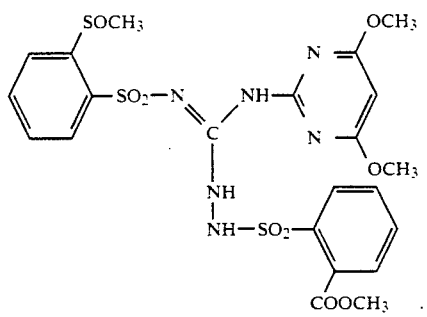

7. A compound according to claim 1, wherein such compound is N'-(4-methyl-pyrimidin-2-yl)-N'-(2-n-butoxycarbonyl-phenylsulphonylamino)-N'''-(2-dimethylaminosulfonylphenylsulphonyl)-guanidine of the formula

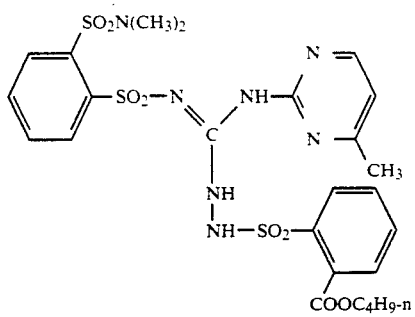

8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidally effective amount of a compound according to claim 1.

10. The method according to claim 9, wherein such compound is
N'-(4-methoxy-6-methyl-pyrimidin-2-yl)-N'-(2-methoxycarbonyl-phenylsulphonylamino)-N'''-(1-methyl-4-ethoxycarbonylpyrazol-5-yl-sulphonyl)guanidine,
N'-(4,6-dimethoxy-pyrimidin-2-yl)-N'-(2-ethoxycarbonyl-phenylsulphonylamino)-N'''-(1-methyl-4-ethoxycarbonylpyrazol-5-yl-sulphonyl)guanidine,
N'-(4,6-dimethoxy-pyrimidin-2-yl)-N'-(2-methoxycarbonyl-phenylsulphonylamino)-N'''-(2-methylmercaptophenylsulphonyl)-guanidine,
N'-(4,6-dimethoxy-pyrimidin-2-yl)-N'-(2-methoxycarbonyl-phenylsulphonylamino)-N'''-(2-methylsulfinylphenylsulphonyl)-guanidine, or
N'-(4-methyl-pyrimidin-2-yl)-N'-(2-n-butoxycarbonyl-phenylsulphonylamino)-N'''-(2-dimethylaminosulfonylphenylsulphonyl)-guanidine.

* * * * *

UNITED STATES PATENT AND TRADEMARK OFFICE
CERTIFICATE OF CORRECTION

PATENT NO. : 5,125,960

DATED : June 30, 1992

INVENTOR(S) : Fest et al.

It is certified that error appears in the above-identified patent and that said Letters Patent is hereby corrected as shown below:

| | |
|---|---|
| Col. 59, line 17 | Before " represents " insert -- $R^1$ -- |
| Col. 59, line 28 | Delete " $R^2$ " and substitute -- $R^9$ -- |
| Col. 59, line 30 | Delete " $C_\alpha-C_3$ " and substitute -- $C_1-C_3$ -- |
| Col. 60, line 22 | Delete " p1 ", start new paragraph before " $R^5$ " |
| Col. 60, line 31 | Delete " N' " and substitute -- N'' -- |
| Col. 60, line 49 | Delete " N' " (second occurrence) and substitute -- N'' -- |
| Col. 60, last line | Delete " N' " (second occurrence) and substitute -- N'' -- |
| Col. 61, line 20 | Delete " N' " (second occurrence) and substitute -- N'' -- |
| Col. 61, line 41 | Delete " N' " (second occurrence) and substitute -- N'' -- |
| Col. 62, line 27 | Delete " N' " (second occurrence) and substitute -- N' -- |
| Col. 62, line 30 | Delete " N' " (second occurrence) and substitute -- N'' -- |
| Col. 62, line 33 | Delete " N' " (second occurrence) and substitute -- N'' -- |

UNITED STATES PATENT AND TRADEMARK OFFICE
CERTIFICATE OF CORRECTION

PATENT NO. : 5,125,960

DATED : June 30, 1992

INVENTOR(S) : Fest et al.

It is certified that error appears in the above-identified patent and that said Letters Patent is hereby corrected as shown below:

Col. 62, lines 36-39   Delete " N' " (second occurrence) and substitute -- N'' --

Signed and Sealed this

Twenty-second Day of February, 1994

Attest:

BRUCE LEHMAN

Attesting Officer  Commissioner of Patents and Trademarks